(12) United States Patent
Alpins

(10) Patent No.: US 9,101,295 B2
(45) Date of Patent: Aug. 11, 2015

(54) ASSESSMENT OF TOPOGRAPHIC SEMI-MERIDIAN PARAMETERS FOR CORNEAL ASTIGMATISM ANALYSIS AND VECTOR PLANNING TREATMENT

(76) Inventor: Noel Ami Alpins, Cheltenham (AU)

( * ) Notice: Subject to any disclaimer, the term of this patent is extended or adjusted under 35 U.S.C. 154(b) by 470 days.

(21) Appl. No.: 13/475,230

(22) Filed: May 18, 2012

(65) Prior Publication Data

US 2012/0229767 A1 Sep. 13, 2012

Related U.S. Application Data

(63) Continuation-in-part of application No. 12/945,764, filed on Nov. 12, 2010, now Pat. No. 8,678,587.

(60) Provisional application No. 61/260,556, filed on Nov. 12, 2009, provisional application No. 61/602,792, filed on Feb. 24, 2012.

(51) Int. Cl.
*A61B 3/10* (2006.01)
*A61B 3/14* (2006.01)
*A61B 3/00* (2006.01)
*A61B 3/107* (2006.01)
*A61F 9/008* (2006.01)
*A61B 3/103* (2006.01)

(52) U.S. Cl.
CPC .............. *A61B 3/107* (2013.01); *A61B 3/0025* (2013.01); *A61F 9/008* (2013.01); *A61F 9/00804* (2013.01); *A61B 3/1035* (2013.01); *A61F 2009/00872* (2013.01); *A61F 2009/00878* (2013.01); *A61F 2009/00882* (2013.01)

(58) Field of Classification Search
CPC .......... A61B 3/103; A61B 3/14; A61B 3/113; A61B 3/1225; A61B 3/024; A61B 3/032; A61B 3/1015
USPC .......... 351/205–206, 210, 221–222, 246, 239
See application file for complete search history.

(56) References Cited

U.S. PATENT DOCUMENTS 6,467,906 B1 * 10/2002 Alpins .......................... 351/212
2003/0025877 A1 * 2/2003 Yancey et al. ................ 351/221
2003/0189690 A1 * 10/2003 Mihashi et al. .............. 351/221

* cited by examiner

*Primary Examiner* — Dawayne A Pinkney
(74) *Attorney, Agent, or Firm* — Ladas & Parry LLP

(57) ABSTRACT

Techniques are disclosed in which a topographic parameter is determined in each hemidivision of the eye by considering the topography of reflected images from a multiplicity of illuminated concentric rings of the cornea. A simulated spherocylinder is produced to fit into each ring and conform to the topography thereof from which a topographic parameter for each ring can be obtained. All of the topographic parameters of each ring are combined and a mean summated value is obtained representing magnitude and meridian of each hemidivision. From these parameters, a single topographic value for the entire eye (CorT) can be found as well as a value representing topographic disparity (TD) between the two hemidivisions. The topography values for the hemidivisions are used in a vector planning system to obtain treatment parameters in a single step operation.

18 Claims, 29 Drawing Sheets

Simulated K Values
42.00D (8.04 mm) @102
41.12D (8.21 mm) @12
Astigmatism: 0.88D
Overall
42.48D (7.94 mm) @290
41.84D (8.07 mm) @90
41.14D (8.20 mm) @24
41.22D (8.19 mm) @158
0-3 mm
41.54D (8.12 mm) @294
41.23D (8.19 mm) @90
40.46D (8.34 mm) @30
40.68D (8.30 mm) @164
3-5 mm
42.45D (7.95 mm) @276
41.87D (8.06 mm) @100
41.13D (8.21 mm) @12
41.17D (8.20 mm) @152
5-7 mm
44.04D (7.66 mm) @260
43.24D (7.81 mm) @66
42.18D (8.00 mm) @4
42.30D (7.98 mm) @158
OD

F I G. 1

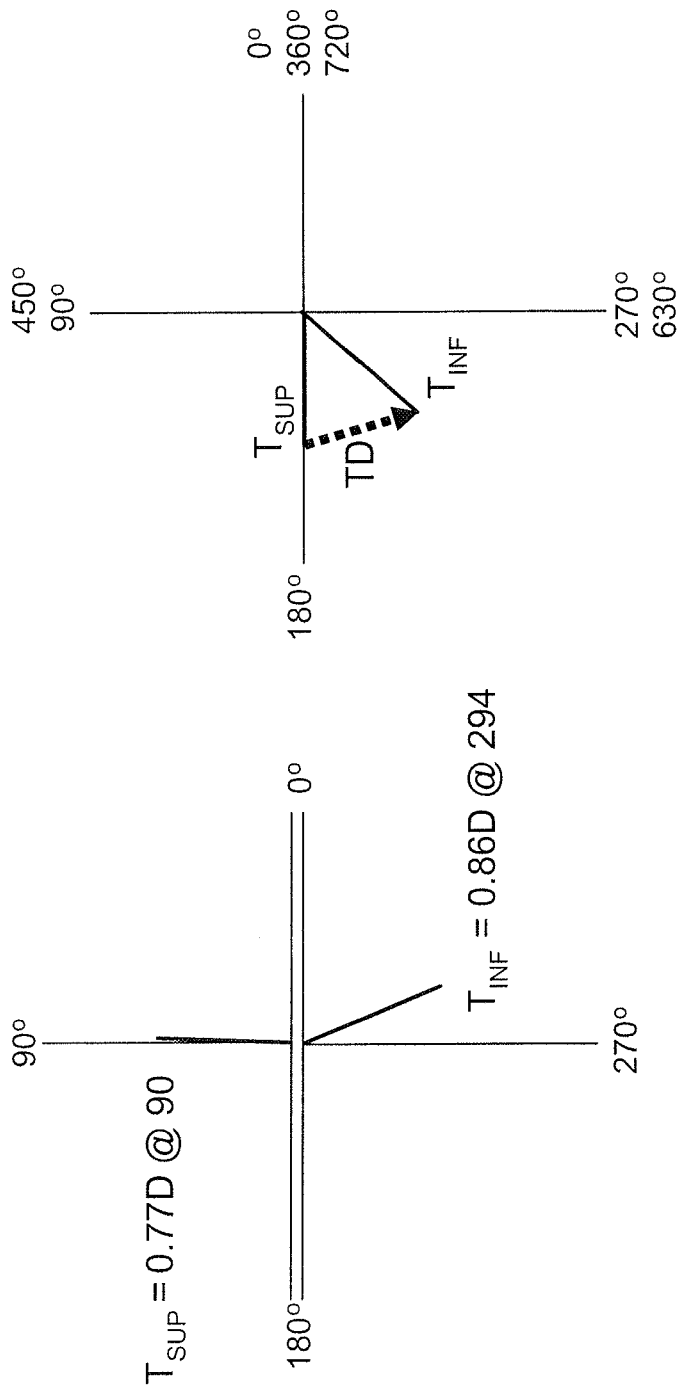

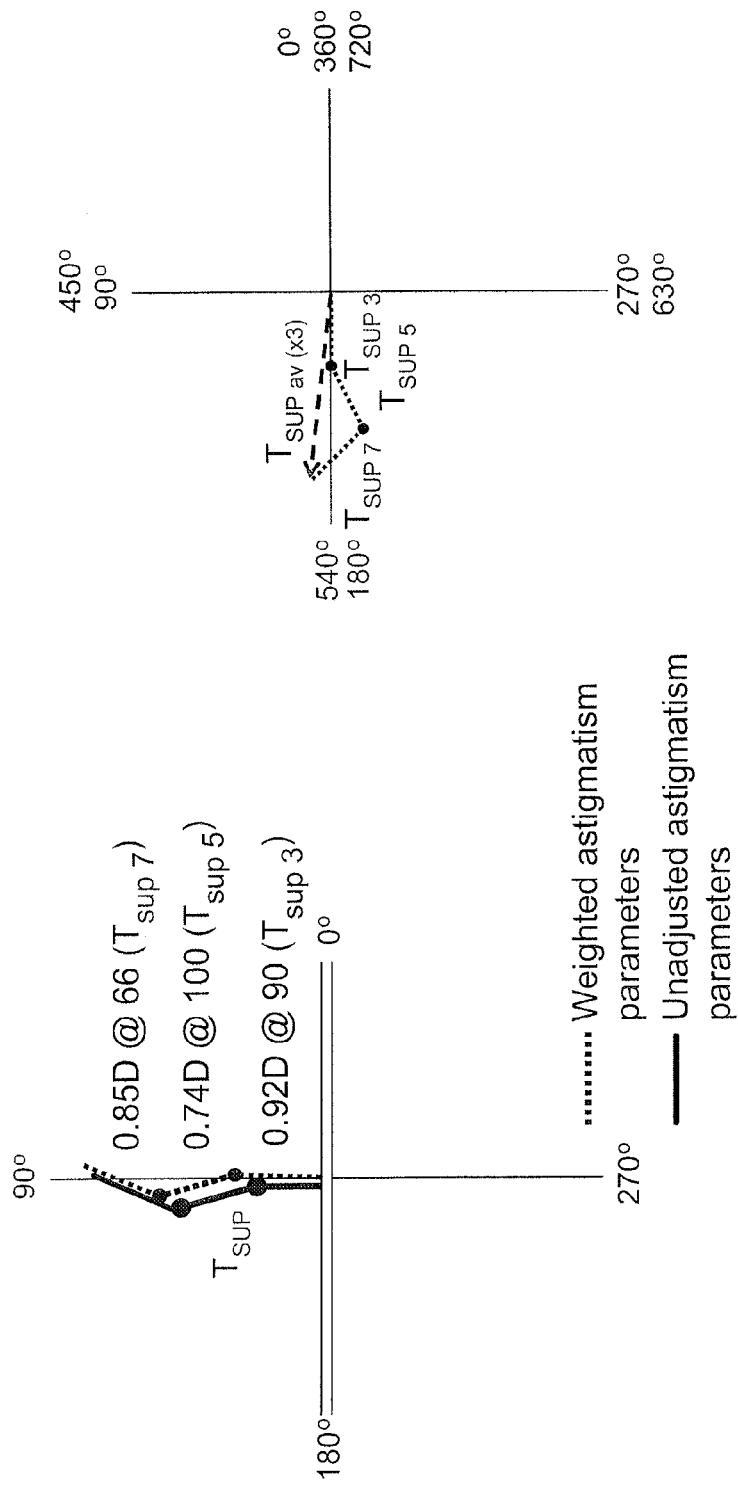

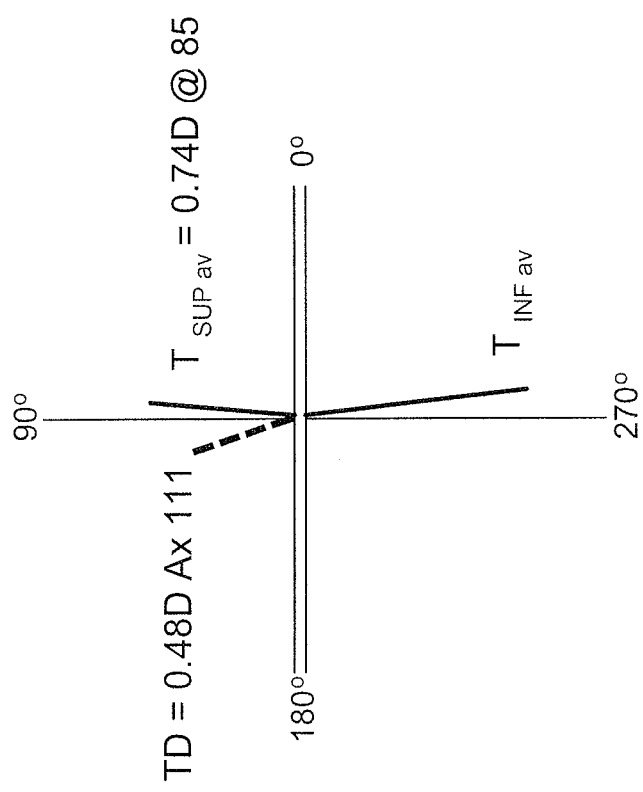

| Zones (mm) Superior | Unadjusted astigmatism (D) | Weighted astigmatism (D) |
|---|---|---|
| 3.0 | 0.77 @ 90 | 0.92 @ 90 |
| 5.0 | 0.74 @ 100 | 0.74 @ 100 |
| 7.0 | 1.06 @ 66 | 0.85 @ 66 |
| $T_{SUP\,av}$ | 0.75 @ 83 | 0.74 @ 85 |
| Zones (mm) Inferior | Unadjusted astigmatism (D) | Weighted astigmatism (D) |
| 3.0 | 0.86 @ 294 | 1.03 @ 294 |
| 5.0 | 1.28 @ 276 | 1.28 @ 276 |
| 7.0 | 1.74 @ 260 | 1.39 @ 260 |
| $T_{INF\,av}$ | 1.16 @ 272 | 1.10 @ 275 |

FIG. 6c

| Cornea (total) | Unadjusted astigmatism (D) | Weighted astigmatism (D) |
|---|---|---|
| TD | 0.50 Ax 106 | 0.48 Ax 111 |
| CorT | 0.95 @ 88 | 0.91 @ 91 |
| Sim K | 0.88 @ 102 | |
| Astigmatism mean (arithmetic) (3, 5, 7mm zones) | 1.08 | 1.04 |

FIG. 6d

| SUPERIOR SEMI-MERIDIAN (all values at corneal plane) | | | |
|---|---|---|---|
| | Topography (D) | Plus Cylinder Refraction (DC) | Minus Cylinder Refraction (DC) |
| Preop | 2.60 @ 130 | +1.63 Ax 108 | -1.63 Ax 18 |
| TIA $_{SUP\ AB}$ | 1.87 Ax 29 | | |

| INFERIOR SEMI-MERIDIAN (all values at corneal plane) | | | |
|---|---|---|---|
| | Topography (D) | Plus Cylinder Refraction (DC) | Minus Cylinder Refraction (DC) |
| Preop | 1.90 @ 278 | +1.63 Ax 288 | -1.63 Ax 198 |
| TIA $_{INF\ AB}$ | 1.71 Ax 194 | | |

| SUPERIOR SEMI-MERIDIAN (AB) | Topography (D) |
|---|---|
| Preop | 2.60 @ 130 |
| TIA $_{SUP\ AB}$ | 1.87 Ax 29 |
| Target T $_{SUP\ B}$ | 1.09 @ 149 |

| INFERIOR SEMI-MERIDIAN (AB) | Topography (D) |
|---|---|
| Preop | 1.90 @ 278 |
| TIA $_{INF\ AB}$ | 1.71 Ax 194 |
| Target T $_{INF\ B}$ | 0.40 @ 250 |

| SUPERIOR SEMI-MERIDIAN (AB) | Wavefront Refraction (DC) |
|---|---|
| Preop | 1.63 Ax 108 |
| $TIA_{SUP\,AB}$ | 1.87 Ax 29 |
| Target $R_{SUP\,B}$ | 0.73 Ax 59 |

| INFERIOR SEMI-MERIDIAN (AB) | Wavefront Refraction (DC) |
|---|---|
| Preop | 1.63 Ax 288 |
| $TIA_{INF\,AB}$ | 1.71 Ax 194 |
| Target $R_{INF\,B}$ | 0.27 Ax 340 |

$$TIA_{NET\ AB\ x1}(1.73\ Ax\ 22) = [TIA_{SUP\ AB}(1.87\ Ax\ 29) + TIA_{INF\ AB}(1.71\ Ax\ 194)] \times 1/2$$

| Calculation of Target $R_B$ (AB) | | |
|---|---|---|
| | Plus Cylinder Refraction (DC) | Minus Cylinder Refraction (DC) |
| Preop | +1.63 Ax 108 | -1.63 Ax 18 |
| $TIA_{NET\,AB}$ | 1.73 Ax 22 | |
| Target $R_B$ | +0.25 Ax 53 | -0.25 Ax 143 |

| ORA$_{SUP\ B}$ (D) | 1.34 Ax 58 |
|---|---|
| ORA$_{INF\ B}$ (D) | 0.24 Ax 358 |

| SUPERIOR SEMI-MERIDIAN (BC) | Topography (D) |
|---|---|
| Preop | 1.09 @ 149 |
| TIA $_{SUP\ BC}$ | 1.34 Ax 58 |
| Target T $_{SUP\ C}$ | 0.25 @ 53 |

| INFERIOR SEMI-MERIDIAN (BC) | Topography (D) |
|---|---|
| Preop | 0.40 @ 250 |
| TIA $_{INF\ BC}$ | 0.24 Ax 357 |
| Target T $_{INF\ C}$ | 0.25 @ 233 |

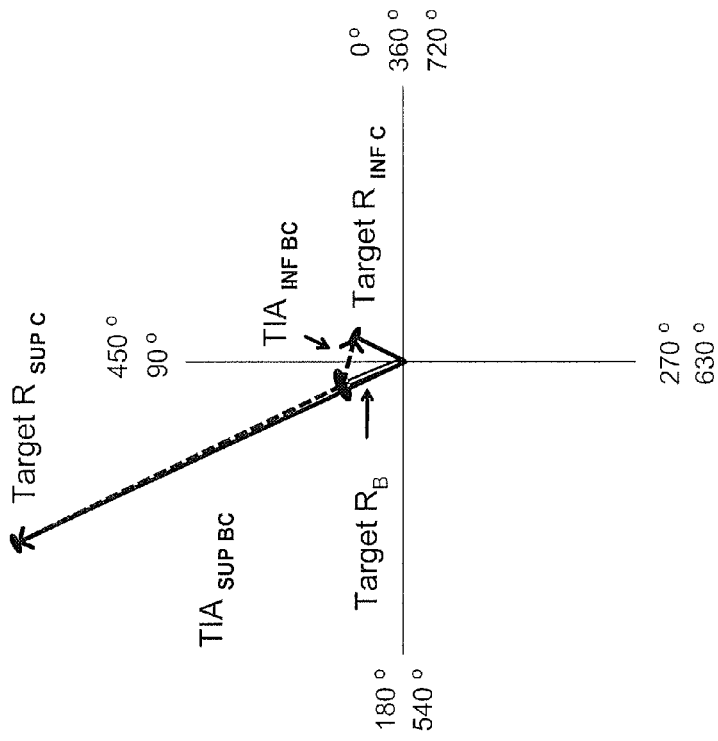
F I G. 12b
| SUPERIOR SEMI-MERIDIAN (BC) | Wavefront Refraction (DC) |
|---|---|
| Preop | 0.25 Ax 53 |
| TIA $_{SUP\ BC}$ | 1.34 Ax 58 |
| Target R $_{SUP\ C}$ | 1.59 Ax 57 |
| INFERIOR SEMI-MERIDIAN (BC) | Wavefront Refraction (DC) |
|---|---|
| Preop | 0.25 Ax 233 |
| TIA $_{INF\ BC}$ | 0.24 Ax 357 |
| Target R $_{INF\ C}$ | 0.27 Ax 206 |

Average TIA$_{NET\ BC}$ (0.62 Ax 53) = [TIA$_{SUP\ BC}$ (1.34 Ax 58) + TIA$_{INF\ BC}$ (0.24 Ax 178)] × 1/2

| SUPERIOR SEMI-MERIDIAN (AC) | Topography (D) |
|---|---|
| Preop | 2.60 @ 130 |
| TIA $_{SUP\ AC}$ | 2.84 Ax 41 |
| Target T$_{SUP\ C}$ | 0.25 @ 53 |

| INFERIOR SEMI-MERIDIAN (AC) | Topography (D) |
|---|---|
| Preop | 0.90 @ 278 |
| TIA $_{INF\ AC}$ | 0.92 Ax 191 |
| Target T$_{INF\ C}$ | 0.25 @ 53 | ic parameter in said eye, and means for combining said target parameters representing topography and said target parameter representing a refractive parameter to produce said surgical parameters representing final treatment target values for the two semi-meridians.

ASSESSMENT OF TOPOGRAPHIC SEMI-MERIDIAN PARAMETERS FOR CORNEAL ASTIGMATISM ANALYSIS AND VECTOR PLANNING TREATMENT

CROSS RELATED APPLICATIONS

The present application is a continuation-in-part of U.S. patent application Ser. No. 12/945,764 filed Nov. 12, 2010 now U.S. Pat. No. 8,678,587, which claims the benefit of U.S. Provisional Application No. 61/260,556 filed on Nov. 12, 2009. The present application also claims the priority of U.S. Provisional Application No. 61/602,792 filed Feb. 24, 2012, the content of which is incorporated herein by reference.

FIELD OF THE INVENTION

The term hemidivision used herein refers to a semi division of the cornea of the eye, in which the superior and inferior hemidivisions make up the total cornea. The term semi-meridian technically refers to the parameters of a hemidivision but is also used as equivalent to the term hemidivision.

The invention relates to the determination of astigmatism parameters to represent each semi-meridian (hemidivision) of the cornea derived from the keratometric view of topography for use in vector analysis and planning of treatment. These two semi-meridian values (for the superior and inferior semi-meridians) can then together determine a single corneal topography value for magnitude and meridian as an alternative to simulated keratometry as well as quantifying the irregularity of the cornea.

The invention further relates to a vector planning modality to simultaneously reduce and regularize naturally occurring irregular corneal astigmatism achieved by applying different laser ablation profiles to each of the two semi-meridians of the cornea. This treatment plan combines both topographic and refractive (wavefront) parameters and can be used as an algorithm for excimer laser technology applications to reduce ocular aberrations and improve visual performance.

The invention further relates to a method and system for quantifying corneal astigmatism that corresponds to manifest refractive cylinder correction better than other commonly used measures of corneal astigmatism. This is of clinical importance when assessing and planning for astigmatism surgery. The technique can also be applied to irregular corneas.

SUMMARY OF THE INVENTION

According to one aspect of the invention, a keratometric map is obtained by computer assisted videokeratography and vector summation is employed to determine two semi-meridian parameters to quantify astigmatism for the separate halves of the cornea. These astigmatism magnitudes can be weighted for 3 mm, 5 mm and 7 mm concentric zones subscribed from the central axis of the cornea so that corneal astigmatism and irregularity can then be quantified. Namely, there are two factors which influence the weighting to be assigned to the 3 mm, 5 mm and 7 mm zones. These are 1) proximity to the central axis of the cornea and 2) the area subscribed by the respective zones. Based on these factors I have found that suitable theoretical weighting coefficients for the 3 mm zone is 1.2, for the 5 mm zone is 1.0 and for the 7 mm zone 0.8. In an evaluation of 100 patients post surgically, it has been found that weighting values for the 3 mm, 5 mm and 7 mm zones are equal, namely 1.0, 1.0, and 1.0 respectively. Subjective evaluation by the surgeon of each individual patient can influence him or her to assign weighting values between these two ranges. Hereafter we will proceed with illustration using the theoretical weighting coefficients 1.2, 1.0, and 0.8 for the 3 mm, 5 mm and 7 mm zones respectively.

The two semi-meridian values calculated using weighting coefficients for the 3 mm, 5 mm and 7 mm zones from topography allow for a more representative determinant of the corneal astigmatism. This provides parameters for the purpose of vector planning treatment and the reliable determination of corneal topographic astigmatism as well as a standard for corneal irregularity. These values can also be used pre and post operatively to gauge the success of astigmatic outcomes in patients undergoing refractive surgery.

In accordance with the invention, there is provided a method for determining parameter of magnitude and axis representing corneal astigmatism for use in vector analysis for diagnostic and surgical treatment, comprising producing a keratometric map of topographic measurements of each of two semi-meridians of the cornea of an eye, assigning weighting values to the topographic measurements in each of a plurality of zones in each semi-meridian, and vectorially combining the weighted values of the topographic measurements to obtain a vector parameter in each semi-meridian representing magnitude and axis of topographic irregularity which is adapted for use in diagnostic and surgical treatment.

In further accordance with the invention, the technique of vector planning combines corneal (topography) and refractive (wavefront) parameters to both reduce and regularize astigmatism in a single treatment step. The treatment is determined by first employing ocular residual astigmatism (ORA) to optimally reduce the astigmatic magnitude, followed by the regularization of the now reduced corneal astigmatism using a common refractive target for the two separate semi-meridians.

The calculated treatments are presented as a single asymmetric treatment application. In this way any astigmatism that cannot be eliminated from the optical system of the eye due to the prevailing ORA is both minimized and regularized.

The advanced vector planning technique of the invention can be used to treat naturally occurring irregular astigmatism by applying the treatment independently to each semi-meridian of the cornea. As a result the remaining astigmatism is optimally minimized and regularized leading to a reduction in ocular aberrations and subsequent potential for improvement in the best corrected visual activity.

Thus, in further accordance with the invention, there is provided a method for reducing and regularizing measured values of astigmatism in an eye of a patient to obtain target values for diagnosis and treatment of the patient, said method comprising the steps of: considering the cornea of an eye of a patient to be divided into superior and inferior semi-meridians; measuring corneal and refractive astigmatism values in each of the semi-meridians; determining topographic treatment parameters in each semi-meridian to maximally reduce the topographic astigmatism values in each of the semi-meridians based on minimizing ocular residual astigmatism in each semi-meridian and regularizing the thus reduced topographic treatment parameters using a common refractive parameter for the two separate semi-meridians to obtain in one step from said determining step to said regularizing step, final treatment target values for the two semi-meridians.

In still further accordance with the invention, there is provided apparatus for carrying out the method of the invention for obtaining surgical parameters comprising: means for obtaining target parameters representing topography of an eye in superior and inferior semi-meridians, means for obtaining a target parameter representing a refractive parameter for each semi-meridian, and a computer means for carrying out the steps of: determining target induced astigmatism vector parameters (TIA) for treating each semi-meridian by vectorially combining the topographic target parameters with the refractive parameter to obtain treatment vectors TIA in the two meridians which are equal and regularized.

A further object of the invention is to provide a method and system that overcomes the deficiencies of the known art.

In further accordance with the invention, there is provided a method in which the eye of a patient is considered to be divided into a multiplicity of concentric rings and at least a portion of the concentric rings of the cornea is fitted with a simulated curved surface that conforms to the topographic surface of each ring in the selected portion of the rings. Corneal parameters are selected on the curved surfaces of each ring and these parameters are vectorially summated to obtain a mean vectorially summated value representing a corneal topographic value of astigmatism for the selected portion of the cornea.

In the case where the selected portion of the cornea is a hemidivision of the eye, the mean vector sum of the rings represents the corneal topographic astigmatism value of the entire hemidivision. By subtracting these values from one another, a measure of the topographic disparity of the two hemidivisions can be determined and by adding these values the corneal topographic astigmatism for the entire eye can be obtained.

In accordance with a particular feature of the invention, the curved surface which is fitted into each ring is a spherocylindrical surface obtained by a method of least squares.

The invention also provides a system for carrying out the methodology described above.

BRIEF DESCRIPTION OF THE DRAWING

FIG. 1 is a topographic illustration of a cornea showing the flat and steep keratometry parameters in the 3 mm, 5 mm and 7 mm zones of the semi-meridians on Humphrey ATLAS topographer.

FIG. 2a is a Polar diagram showing the superior and inferior semimeridian astigmatism values (unadjusted) for the 3 mm zone. (Scale×2).

FIG. 2b is a double angle vector diagram in which astigmatism meridia is doubled for the 3 mm zone while magnitude remains the same and vectorial difference represents topographic disparity (TD) magnitude. (Scale×2)

FIG. 3a is a Polar diagram showing weighted and unadjusted astigmatism parameters for each of the 3 mm, 5 mm and 7 mm semi-meridians in the corresponding superior half of the cornea.

FIG. 3b is a double angle vector diagram showing head to tail summation of the 3 mm, 5 mm and 7 mm weighted astigmatism parameters which are now doubled in angle to calculate the average superior astigmatism parameter.

FIG. 5c is a Polar diagram showing the superior and inferior average astigmatisms from weighted parameters in corresponding corneal semi-meridians. (Scale ×2). The TD is also displayed.

FIG. 6c is a tabular illustration showing the comparative effect of weighted and unadjusted astigmatisms for each zone of the superior and inferior semi-meridians.

FIG. 6d is a tabular illustration showing comparison between CorT and Sim K parameters.

FIG. 12b is a double angle vector diagram showing the refractive targets achieved (Target R) after applying the treatment for the regularization of non-orthogonal astigmatism to the common refractive target (Target $R_B$) achieved from the maximum treatment of astigmatism (step AB).

DETAILED DESCRIPTION OF THE INVENTION

Advances in computer assisted videokeratography (CAVK) have assisted the surgeon by providing detailed information regarding corneal shape. The keratometric view provided by topographers (FIG. 1) displays the corneal power and radius of curvature for different concentric zones of the cornea and provides more information than currently necessary for lasers that provide symmetric refractive corneal treatments. The keratometric view also customarily provides a Simulated Keratometry (Sim K) value that is a quantitative descriptor of corneal astigmatism at the 3 mm zone as an attempt to gain equivalence of corneal keratometry at the time of the introduction of the CAVK technology in the 1980's.

One commonly encountered difficulty with the Sim K value is that the algorithm that selects the meridian can on occasions be erratic where the bow tie demonstrates non-orthogonal characteristics. The topography device may be inconsistent in its choice of meridian ranging from either of the bow tie meridian or somewhere in between. The technique herein provides relevance and consistency in the corneal topography astigmatism value (CorT) by obtaining a vector summated mean magnitude and meridian from the keratometric view at three (inner, middle and peripheral) zones.

Currently no consistent values are offered by topographers that usefully represent the two semi-meridians of the cornea. Nor is there one astigmatism value that represents the whole cornea other than just the paracentral 3 mm region utilized by the Sim K magnitude and meridian value. These two vector semi-meridian values are necessary and useful parameters to derive this single value quantifying the astigmatism of the whole cornea. They are also essential for the vector planning of the asymmetric treatment process, to gauge irregularity and quantify the success of astigmatic outcomes by corneal parameters. The invention seeks to derive these values from the data currently available from corneal topographer maps as seen in FIG. 1.

Using the keratometric parameters from the 3 mm, 5 mm and 7 mm zones circumscribed from the central axis of the cornea (i.e., the area from 0-3 mm, from 3-5 mm and from 5-7 mm respectively), the semi-meridian values can be refined to more reliably identify the meridian and magnitude of the corneal topographical astigmatism by the process of vector summation.

Figure 2C:
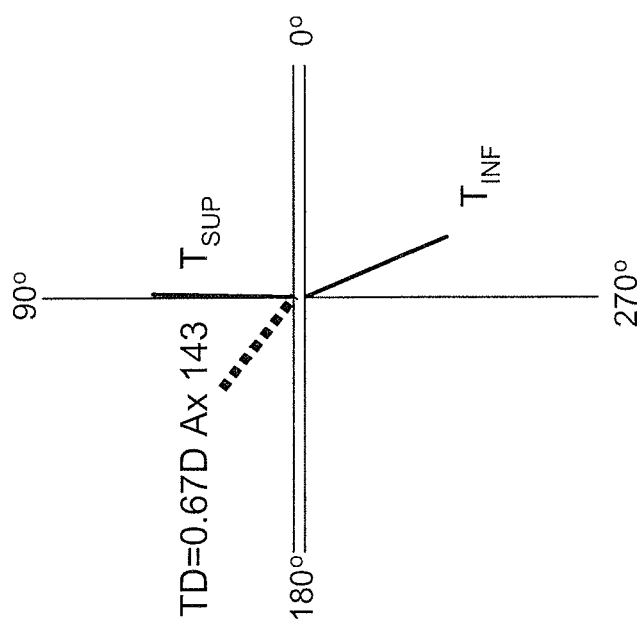
FIG. 2c is a Polar diagram in which the TD axis for the 3 mm zone is divided in half to display the direction as it would appear on the eye. (Scale×2)

The topographic map in FIG. 1 displays two flat and two steep keratometric magnitudes together with their respective meridians for each of the three zones. The most applicable topographic reading for planning treatment and assessing potential astigmatic outcome is that of the 3 mm zone, as this is what predominantly coincides with the pupil and visual axis. Pairing up the most appropriate keratometric parameters for the 3 mm zone is determined by establishing the minimum magnitude of corneal irregularity or TD of the two pairs. That is, using one combination of flat/steep to determine the TD and comparing this in magnitude to the other combination of flat/steep to find the minimum of the two choices (FIGS. 2a, b and c).

Once the appropriate pairing is established for the 3 mm zone, the corresponding steep meridian in the 5 mm zone is determined by calculating the smallest angular difference between each of the steep meridians in the 5 mm zone relative to the 3 mm steep meridian determined from step 1 above. This is then repeated for the 7 mm zone, comparing the angular difference to the parameters of the 5 mm zone. The same process is then applied for the flat meridian. The magnitude of astigmatism for each zone is determined by the arithmetic difference between the flat and steep parameters for that zone, and its orientation is that of the steepest meridian.

Figures 4A, 4B:
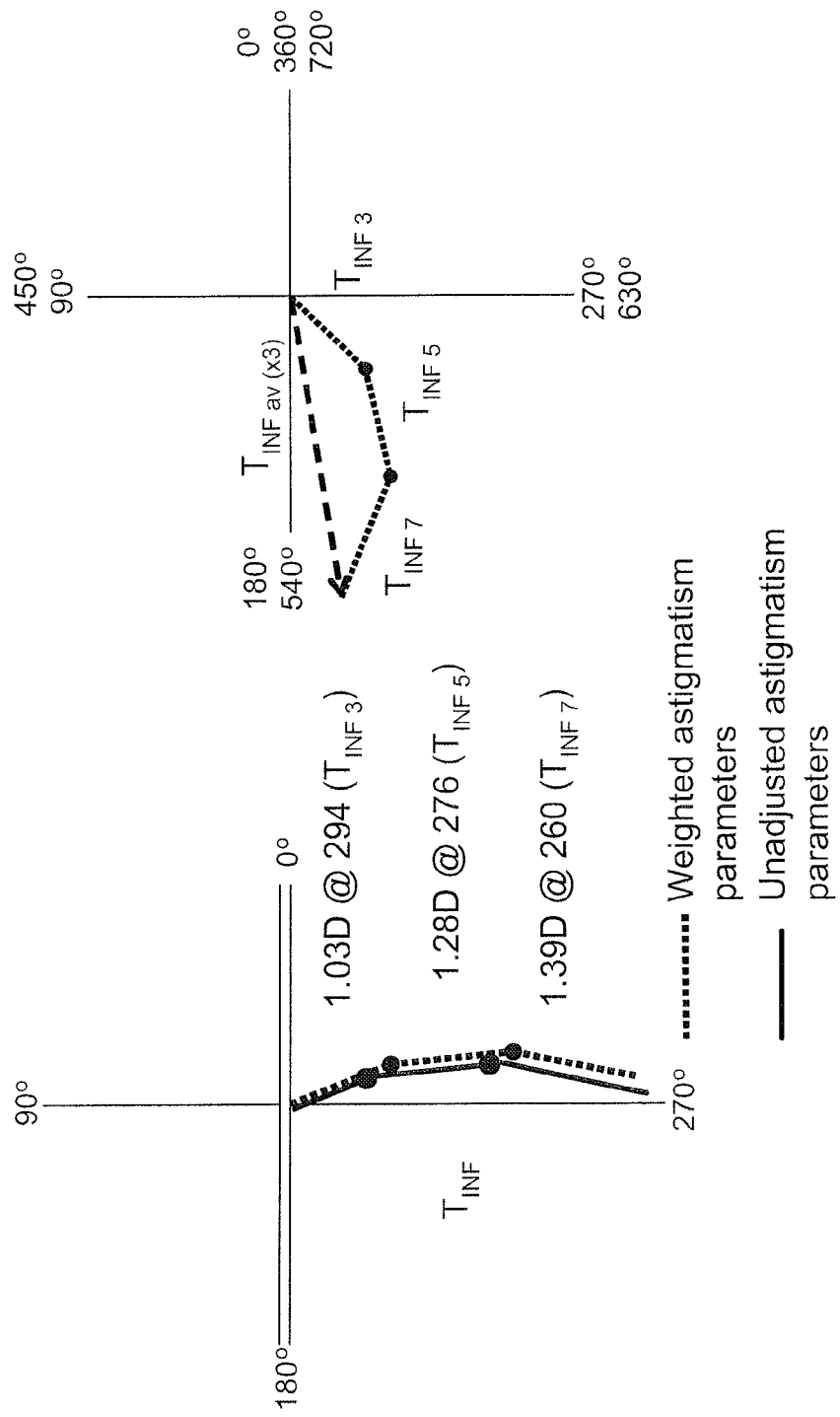
FIG. 4a is a Polar diagram showing weighted and unadjusted astigmatism values for each of the 3 mm, 5 mm and 7 mm semi-meridian in the corresponding inferior half of the cornea.
FIG. 4b is a double angle vector diagram showing a head to tail summation of the 3 mm, 5 mm and 7 mm weighted astigmatism parameters which are now doubled in angle to calculate the average inferior astigmatism parameter.

The result is three astigmatism values for the superior semi-meridian of the cornea (3, 5 and 7 mm zones) and three for the inferior semi-meridian of the cornea (3, 5 and 7 mm zones). Based on the significance of the 3 mm, 5 mm and 7 mm zones in any surgical treatment paradigm, a weighting can be given to each zone, suitably increased for the inner and reduced for the outer with the middle unchanged: ×1.2 for the 3 mm (most applicable), ×1.0 for the 5 mm and ×0.8 for the 7 mm zone (least applicable) (FIGS. 3a and 4a).

Figure 5B:
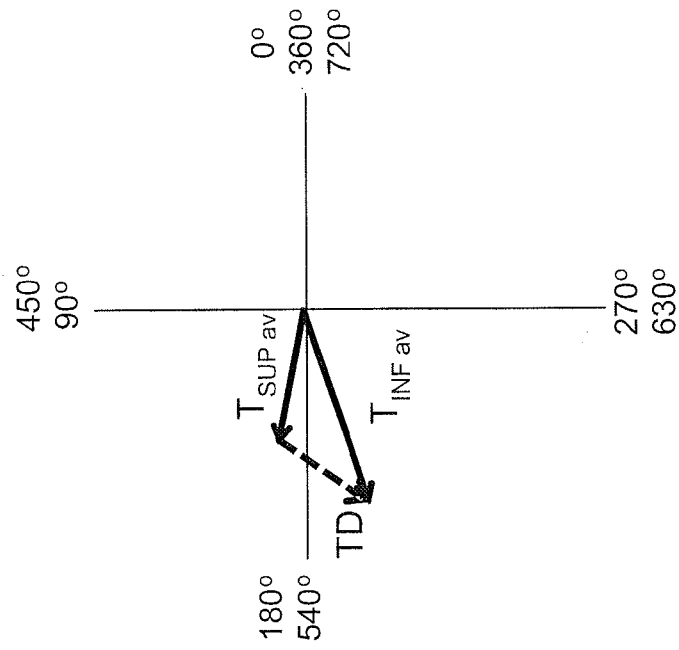
FIG. 5b is a double angle vector diagram showing the vectorial difference between superior and inferior average weighted astigmatisms which in calculated to be the TD (DAVD). (Scale×2)
Figure 5A:
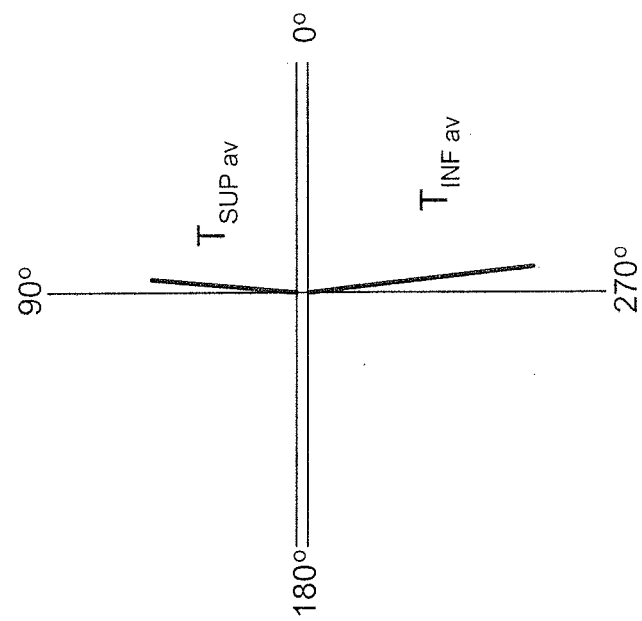
FIG. 5a is a Polar diagram showing the average superior and inferior weighted semi-meridian astigmatism values. (Scale×2)

The polar diagram in FIG. 5a displays the two summated vector means as they would appear on an eye-one astigmatism in the superior semi-meridian and another in the inferior semi-meridian. These topographic astigmatism values will be used in vector planning as will be described later.

To determine the irregularity of the whole cornea, factoring in the weightings for the 3, 5 and 7 mm zones discussed above, the vectorial difference between these two astigmatisms is calculated by again doubling the axis on to a DAVD (FIG. 5b). The final meridian of the TD is determined by joining the resultant vector originating from the superior average astigmatism and terminating at the inferior average astigmatism on the DAVD and then being returned to the origin and halved to determine its actual direction. The corneal irregularity quantified in this way is termed Topographic Disparity (TD) and is expressed in diopters and degrees. This provides the value as it would appear on an eye (FIG. 5c).

Figures 6A, 6B:
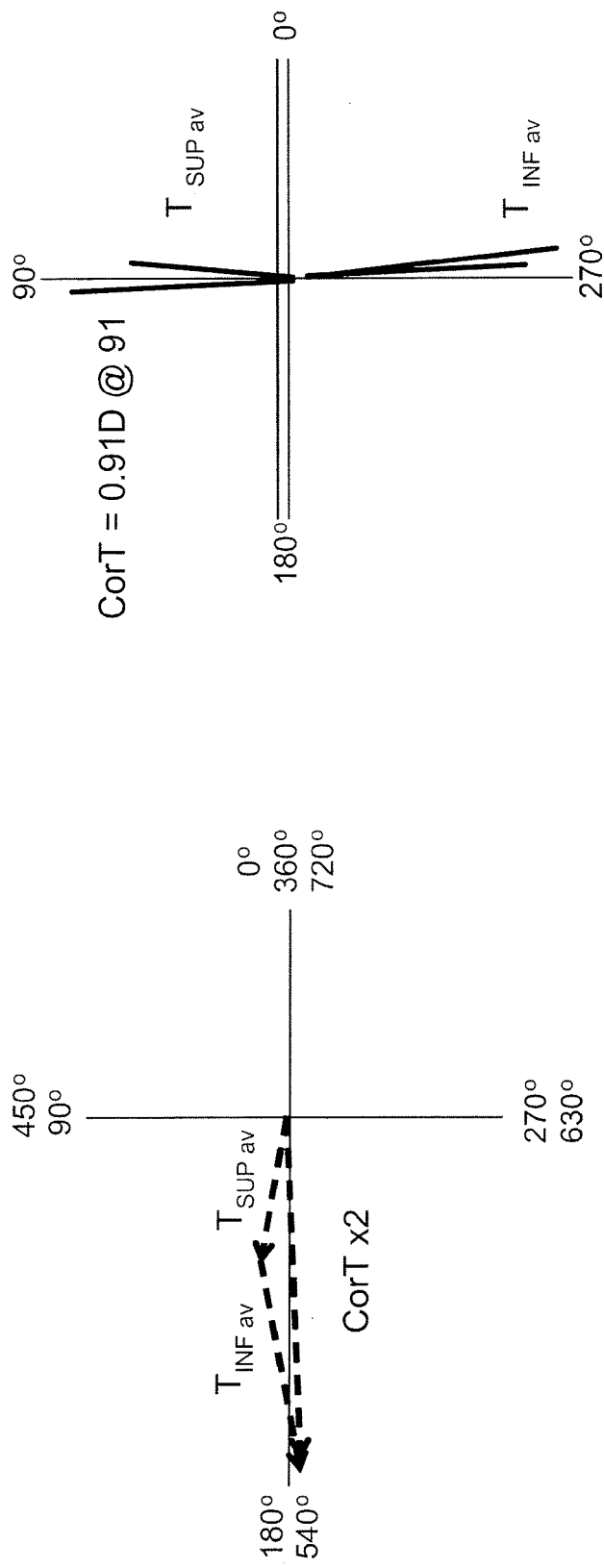
FIG. 6a is a double angle vector diagram showing the vector summation of the superior and inferior average weighted astigmatism values representing CorT (DAVD).
FIG. 6b is a Polar diagram showing the superior and inferior average weighted astigmatism values together with the CorT.

To determine the total corneal topography astigmatism (CorT) as a representation of the whole cornea, a vector summated mean is calculated using the T sup and $T_{INF}$ weighted values (FIGS. 6a and 6b). This describes the whole cornea as quantified by corneal topography with appropriate weightings to the 3, 5 and 7 mm zones such as presented in the example. This is preferential to the simulated keratometry value (Sim K) which is derived entirely from the 3 mm zone with variability and inconsistent bias sometimes demonstrated in the meridian selected.

The concentric corneal zones provided by the topography map (i.e. at 3 mm, 5 mm and 7 mm) are used to achieve two semi-meridian values, each representing one half of the cornea, and to weight the relevance of each zone and then determine corneal irregularity. This technique assesses the topographic disparity (TD)—a vectorial measure of irregular astigmatism, calculated as the dioptric distance between the displays of superior and inferior values on a 720 degree double-angle vector diagram (DAVD). A direct proportional relationship between increasing TD and ocular residual astigmatism (ORA) has been observed.

The ORA which quantifies the internal aberrations of the eye is calculated as the vectorial difference between corneal and refractive astigmatism parameters, and has a magnitude expressed in diopters and an orientation in degrees.

The relationship between TD and ORA has been shown to be significant in a group of 100 healthy astigmatic corneas prior to surgery. ORA and TD magnitudes of 0.75 D or less are considered to be normal with no impediment to achieving good astigmatic outcomes. Whereas magnitudes above 1.00 D might display a significant concern for the excess degree of internal aberrations or corneal irregularity with potential adverse outcomes, so that refractive laser or incisional surgery to correct astigmatism may be limited in the outcome achievable in correcting astigmatism. For this reason the surgeon may decide not to treat or to use vector planning as a treatment paradigm to optimize and reduce the resultant amount of corneal astigmatism remaining in such cases.

FIG. 6c displays the importance of the weighted summated vector means ($T_{SUPav}$ and $T_{INFav}$). The 7 mm zone unadjusted astigmatism magnitude is comparatively large at 1.74 D for the inferior semi-meridian, relative to the corresponding 1.06 D for the superior semi-meridian. In both the superior and inferior semi-meridian the 7 mm astigmatism values are larger than the 3 mm and 5 mm ones for the unadjusted parameters. The importance of a summated average vector is highlighted by the 'dampening' down of 0.06 D for the inferior semi-meridian, but only 0.01 D for the superior semi-meridian.

The summated vector mean of the two weighted semi-meridian values $T_{SUP\ av}$ and $T_{INF\ av}$ can be determined (FIG. 6d) to calculate an effective total corneal topography astigmatism described here as the CorT value (0.91 D @ 91). Examining the relationship of the Sim K (0.88 D @ 102) to the CorT value reveals similar magnitudes (both less than the arithmetic mean) this is likely a similar effect estimating the corneal topography astigmatism as a result of the steep meridian of the three zones not being inline. The meridian of the CorT value however aligns closer to the $T_{SUP}$ (85 degrees) and $T_{INF}$ (275 degrees) in a clockwise direction and as a result is likely more representative of the total corneal astigmatism meridian by factoring in the influence of the 7 mm zone orientation. This difference of almost 10 degrees (CorT meridian of 91 degrees compared to Sim K meridian of 102 degrees) would be a significant amount to factor in during surgical incision or laser planning.

It is important to note that the greater the lack of linearity of each of the individual components in the three zones, the less the effective regular astigmatism represented by Sim K or CorT. The values of 20% increase and decrease from unity for the inner and outer zones respectively is an example which is empirically estimated at this stage and could be modified in the future according to experience and population studies. The sum of the three weighted zone values of 3.0 D is equal to the sum of the three unadjusted unity values so that no net increase or decrease of astigmatism results from this adjustment process.

The closeness of the Sim K magnitude and weighted CorT magnitudes also demonstrates the parallel effect of this non linear phenomenon, and how effectively the CorT represents the whole cornea. Of particular benefit of CorT is accuracy and consistency in identifying the most relevant meridian by employing the vectorial sum and mean of the Tsup and TINF semi-meridian components.

The technique provides additional safety where corneal parameters are included in the refractive treatment plan using vector planning. Vector averaging of multiple values reduces the effect of any measurement artefact or actual outliers that may occur in an automated measurement process such as CAVK.

This method of calculating semi-meridian values to quantify corneal astigmatism incorporates the keratometric magnitudes and meridian of each of the 3 mm, 5 mm and 7 mm zones from both halves of the cornea. These two semi-meridian values can in turn undergo vector summation to provide a corneal topography astigmatism value—the CorT that quantifies the overall corneal astigmatism of the eye as determined by corneal topography. This value may have benefits over Sim K values currently employed. The semi-meridian values calculated can also provide a vectorial value for corneal irregularity—the topographic disparity. This together with the ORA value, can be used in the consulting suite as fundamental preoperative parameters to determine patient suitability and potential for good visual outcomes when planning refractive surgery to correct for astigmatism.

The technique described also allows for adjusted weighting to be given to values closer to or further from the visual axis, by providing a factor to apportion greater or lesser relevance to their magnitudes at the measured meridian. The derived semi-meridian values, each representing one half of the cornea, can be incorporated as treatment parameters to accurately quantify the corneal astigmatism required to resolve with refractive parameters in the vector planning treatment process. Combining corneal and refractive parameters in the vector planning process for the concurrent treatment of idiopathic irregular astigmatism using these semi-meridian values, can potentially lead to greater consistency in corneal astigmatism outcomes, providing the opportunity for further refinement of overall visual outcome quality in the routine laser vision correction process.

Using the parameters in FIG. 1:

Step 1. Determine the appropriate pairing of flat and steep meridian.

(i) To determine the appropriate pairing of flat and steep parameters calculate the minimum TD magnitude from the values in the 3 mm zone.

First pairing (FIGS. 2a, 2b and 2c)—
40.46/41.23 @ 90 (0.77 D @ 90) superior semi-meridian
40.68/41.54 @ 294 (0.86 D @ 294) inferior semi-meridian
TD=0.67 D
Alternative pairing—
40.68/41.23 @ 90 (0.55 D @ 90) superior semi-meridian
40.46/41.54 @ 294 (1.08 D @ 294) inferior semi-meridian
TD=0.82 D
The first pairing has the lower irregularity value so is selected to provide adjusted astigmatism values for zones.

Step 2. Apply the appropriate weightings to the flat/steep parameters selected from (i). (FIGS. 3a and 4a)

3 mmzone:

0.77 D @ 90 (superior semi-meridian)×1.2 (weighting for 3 mm zone)=0.92 D@90

0.86 D @ 294 (inferior semi-meridian)×1.2 (weighting for 3 mm zone)=1.03 D @294

Step 3. Match up the corresponding steep and flat keratometry readings in the 5 mm zone by selecting the ones closest by angular separation to that in the 3 mm zone.

5 mm zone:

41.13/41.87 @ 100 (0.74 D @ 100) superior semi-meridian 0.74 D @ 100×1.0 (weighting for 5 mm zone)=0.74 D @ 100

41.17/42.45 @ 276 (1.28 D @ 276) inferior semi-meridian 1.28 D @ 276×1.0 (weighting for 5 mm zone)=1.28 D @ 276

Step 4. Again match up the corresponding steep and flat keratometry readings for the 7 mm zone by selecting the ones closest by angular separation to that in the 5 mm zone.

7 mmzone:

42.18/43.24 @ 66 (1.06 D @ 66) superior semi-meridian 1.06 D @ 66×0.80 (weighting for 7 mm zone)=0.85 D @ 66

42.30/44.04 @ 260 (1.74 @ 260) inferior semi-meridian 1.74 D @ 260×0.80 (weighting for 7 mm zone)=1.39 D @ 260

Step 5. Head-to-tail summation is used to calculate the resultant superior and inferior semi-meridian average astigmatism (FIGS. 3b and 4b).

Summated vector mean superior astigmatism=0.74 D @ 85 $T_{SUPav}$

Summated vector mean inferior astigmatism=1.1 OD @ 275 $T_{INFav}$ (FIG. 5a).

Step 6. Vectorial difference $T_{SUP}$ and $T_{INF}$.

Doubling the meridian of the average superior and inferior vector mean astigmatism ($T_{SUP\ av}$ and $T_{INF\ av}$ and determining the vectorial difference on a DAVD provide the corneal irregularity or TD in diopters and degrees.

TD=0.48 D Ax 111 (FIGS. 5b and 5c).

Step 7. Vectorial addition $T_{SUP}$ and $T_{INF}$ for CorT value.

Head to tail summation of superior and inferior astigmatism values to derive a corneal topography astigmatism value (CorT) which is represented on both semi-meridian with equal magnitudes and 180 apart.

0.91 D @91

0.91 D @271

Significant ocular aberrations can reduce the quality and quantity of vision resulting in symptoms of glare, haloes, star bursting of light at night and an overall reduction in best corrected visual acuity. These commonly occur in cases of irregular astigmatism and can be measured in quantified by aberrometry. An accurate gauge of aberrations can also be calculated by vectorial differences in corneal and refractive astigmatic values to quantify the internal (non-corneal) aberrations.

The technique of vector planning is a systematic paradigm that enables the combination of corneal parameters with refractive parameters for the optimized treatment of astigmatism.

Advanced vector planning allows for treatment of naturally occurring irregular astigmatism using LASIK or PARK for each semi-meridian of the cornea. The process provides potential for improvement in visual outcomes over the exclusive use of either topographic or wavefront refractive values.

There is commonly a difference between corneal and refractive astigmatism magnitudes and/or axes. In such cases this is quantified by the ocular residual astigmatism (ORA) The ORA is a calculated vectorial value that quantifies intraocular aberrations due to differences between topographical and second order aberrometry astigmatism. Higher amounts of ORA are directly proportional to larger amounts of topographic disparity (TD) as previously shown as a calculated vectorial value to quantify corneal irregularity. Reducing ocular aberrations by minimizing the resultant ORA using vector planning can improve the visual performance of an eye.

The technique of applying vector planning independently to each semi-meridian of the cornea is described hereafter.

To further improve current astigmatic and visual outcomes in excimer laser surgery two treatment principles are paramount. Firstly, the total sum astigmatism as examined both topographically and refractively is maximally reduced (which will be a minimum value quantified by the ORA). Secondly, the minimum astigmatism remaining on the cornea is preferentially left in a regular state. These two principles have heretofore been separately detailed for naturally occurring regular and irregular astigmatism.

Vector planning enables maximum reduction of astigmatism in such a way that the sum of the resultant topographic and refractive astigmatic targets (i.e. the ORA) is at a minimum for that individual eye's unique parameters. This remaining astigmatism is best apportioned between the topographic and refractive modalities in an optimized manner. The net effect is to leave less astigmatism remaining on the cornea and potentially achieve a better visual outcome with reduced lower and higher order optical aberrations.

Naturally occurring irregular astigmatism is widely prevalent in the population presenting for laser surgery and can be quantified using the TD evaluation. This vectorial value has a magnitude and axis, and is expressed in diopters as previously explained with 43% of eyes in a previous study having a value of greater than 1.00 D. It is calculated as the separation between the two opposite semi-meridian astigmatic values representing each half of the topography map on a 720 degree double angle vector diagram (DAVD) (FIGS. 1a, b and c). Note the relevant direct relationship observed that the higher the irregularity (TD) of a cornea the greater is the ORA.

To maximally reduce the astigmatism, one common value for refractive astigmatism (manifest or wavefront) can be resolved separately with two differing topographic astigmatism values; one for each semi-meridian of the cornea as shown, for example, in FIGS. 6a to d. FIG. 6d shows CorT as an arithmetic average of $T_{SUP\ A}$ and $T_{SUP\ A}$ which best represents the corneal astigmatism using the weighted 3 mm, 5 mm and 7 mm values. Current modes of practice using wavefront or manifest refraction only ascertain a single refractive cylinder value for the entire eye including the cornea. The additional step of regularization of the resultant reduced but still irregular corneal astigmatism is beneficial to achieve an orthogonal and symmetrical cornea and hence achieve the best visual potential for an eye.

The treatment process, according to the invention, sequentially combines the two fundamental treatment steps into one. Firstly, maximally and optimally reducing the astigmatism (step from A to B) employing both topographic and wavefront parameters in an optimized manner, followed secondly by the regularization of the remaining corneal astigmatism (step from B to C); these two separate steps can be merged into a single step treatment process, calculated at the final orthogonal symmetrical targets C from the preoperative astigmatism state of A.

Treatment Paradigm For Naturally Occurring Irregular Astigmatism

1. The Optimal Reduction of Astigmatism (step A to B).

Figure 7B:
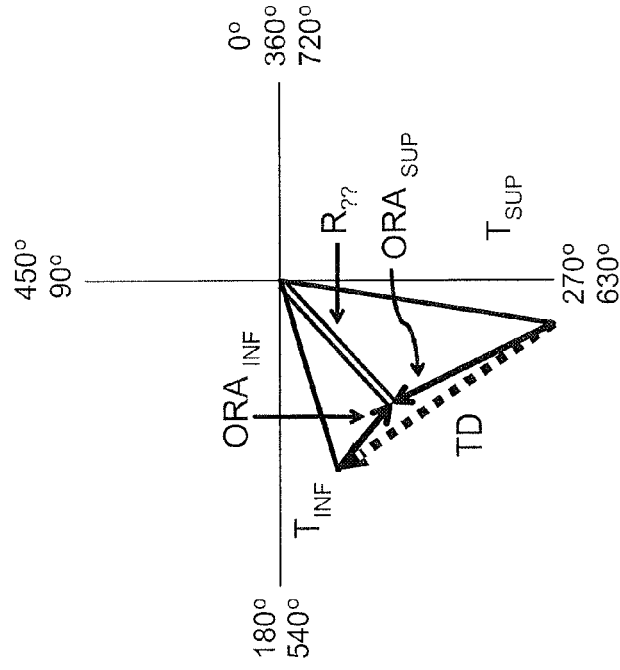
FIG. 7b is a double angle vector diagram showing the parameters of FIG. 7a as vectors displayed at 2× angle.
Figure 7A:
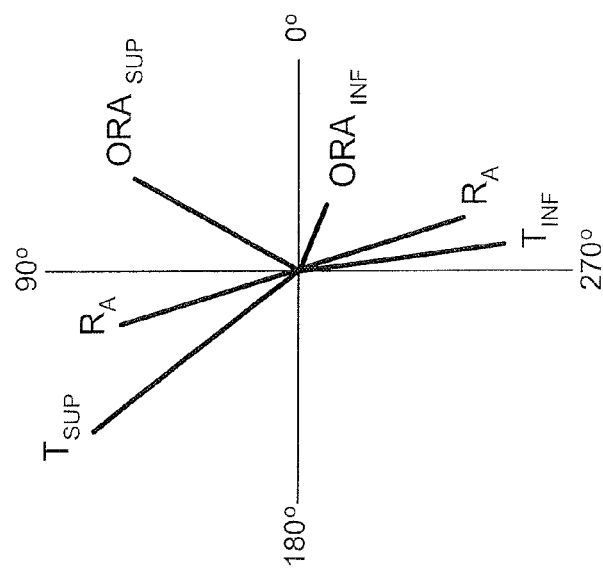
FIG. 7a is a polar diagram illustrating topographic disparity (TD) representing vectorial measure of irregularity as it would appear on the eye.
Figure 7C:
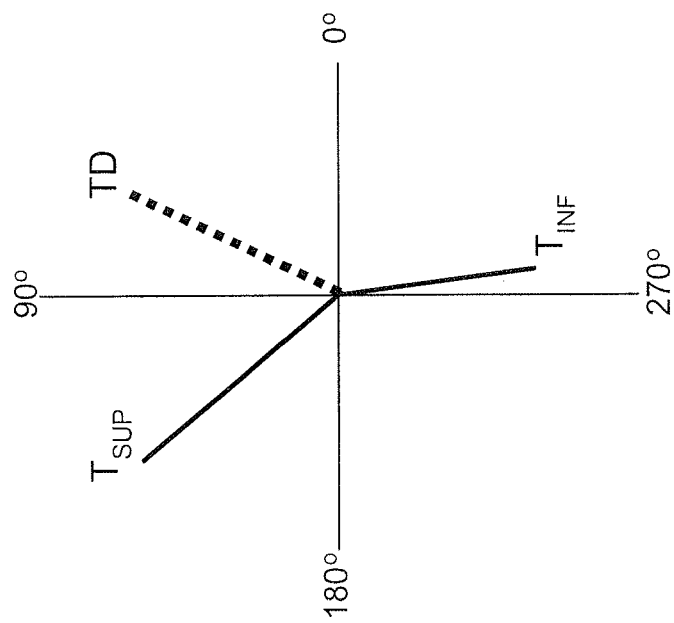
FIG. 7c is a polar diagram illustrating topographic disparity (TD) representing a vectonal measure of irregularity as it would appear on the eye.

FIG. 7a displays a 360 degree polar (not vector) diagram of astigmatism parameters as measured by topography and refraction, in which the two pre-operative measurements do not correspond with each other in magnitude or orientation. The corneal astigmatism is irregular as the superior topographic semi-meridian value ($T_{SUP}$) differs from the inferior topographic semi-meridian value ($T_{INF}$) both in magnitude and orientation as shown in FIG. 6, hence making it both asymmetrical and non-orthogonal. The refractive astigmatism (R), using wavefront (second order Zernike 3 and 5 cylindrical astigmatism) or manifest parameters, is displayed as a common symmetrical orthogonal value for the superior and inferior corneal semi-meridians.

Calculation of the ORA

The first parameter that requires calculation to maximally reduce the existing astigmatism is the ORA—this is the vectorial difference between the refractive and corneal astigmatism at the corneal plane.

The existing astigmatism can be quantified by the simple arithmetic sum of the refractive and topographic components. This quantifies the sum total astigmatism to be corrected, and what proportion is uncorrected as quantified by the ORA. In the presence of corneal irregularity, the ORA can be calculated separately for each of the two semi-meridian s as shown in FIG. 7a wherein the ORA is the vectorial difference between the topographic and refractive parameters for each semi-meridian. The neutralization of the ORA must occur either on the cornea or in the spectacles, or in this case where operative parameters are optimized, a combination of the two (FIG. 8 displays the corresponding treatment vectors). The emphasis chosen here for apportioning correction of the ORA is 40% topographic and 60% refractive this has previously been calculated as an average and used in a vector planning study.

The apportioning of each can vary from case to case and is dependent on the proportional theoretical topographic and refractive targets the surgeon is aiming to achieve. Where possible these targets should aim at reducing the corneal astigmatism to 0.75 D and the spectacle refraction cylinder to 0.50 DC or less. In cases where this is not achievable because the ORA is greater than 1.25 D then another emphasis option as previously may be appropriate. Regardless of the emphasis placed on how to optimally deal with the ORA, the maximum amount of astigmatism is being treated in the optical system of any eye when the sum of the topography and refractive astigmatism targets equal the ORA. Calculating the ORA prior to surgery allows the maximum amount of astigmatism to be treated and the amount left on the cornea minimized to more acceptable levels.

Figure 9A:
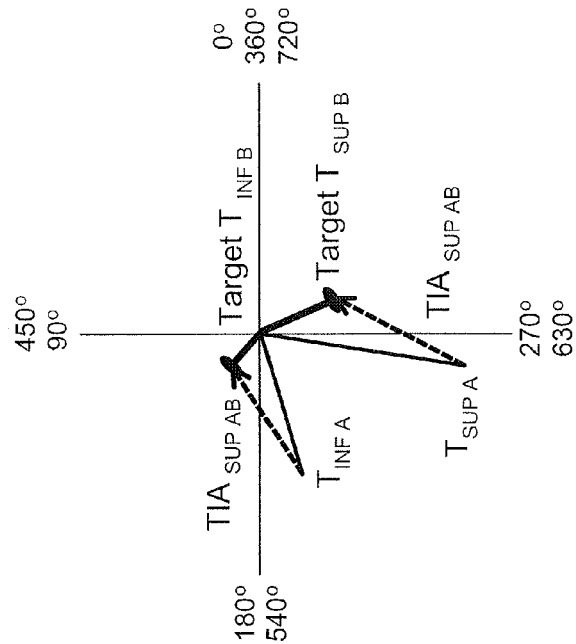
FIG. 9a is a double angle vector diagram showing the component in FIG. 8 with their magnitudes and axis.
Figure 9B:
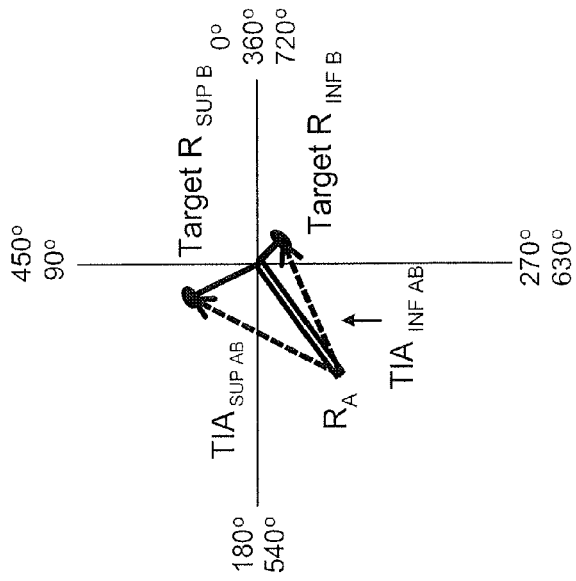
FIG. 9b is a double angle vector diagram after treatment of the components along with respective magnitudes and axes.

Calculation of Treatment (TIA) to Optimally Reduce Astigmatism with Minimum ORA Remaining The target induced astigmatism vector (TIA) for astigmatic treatment for each semi-meridian is a steepening effect and hence is aligned with the axis that is being maximally ablated. The TIA is the vectorial difference, or the treatment required between the preoperative astigmatism and the target which it identifies. This treatment vector can be applied separately, to each semi-meridian $TIA_{SUP\ AB}$ and $TIA_{INF\ AB}$ differing both in magnitude and meridian due to the differing topographic values T representing each semi-meridian. This can be represented on a DAVD—that is, the TIA vectors are doubled in axes with no change in magnitude and then applied to their corresponding preoperative topography values (on the DAVD at two times their steep meridian). This results in topographic targets (Target $T_{SUP\ B}$ and $T_{INF\ B}$) of the astigmatic reduction from A to B which still remain asymmetrical and non-orthogonal (FIG. 9a). The same process can be applied to the common refractive astigmatism using the treatment vectors $TIA_{SUP\ AB}$ and $TIA_{INF\ AB}$ to achieve two refractive targets (FIG. 9b)—one for each semi-meridian—although in practice only one refractive target is utilized.

Figure 10:
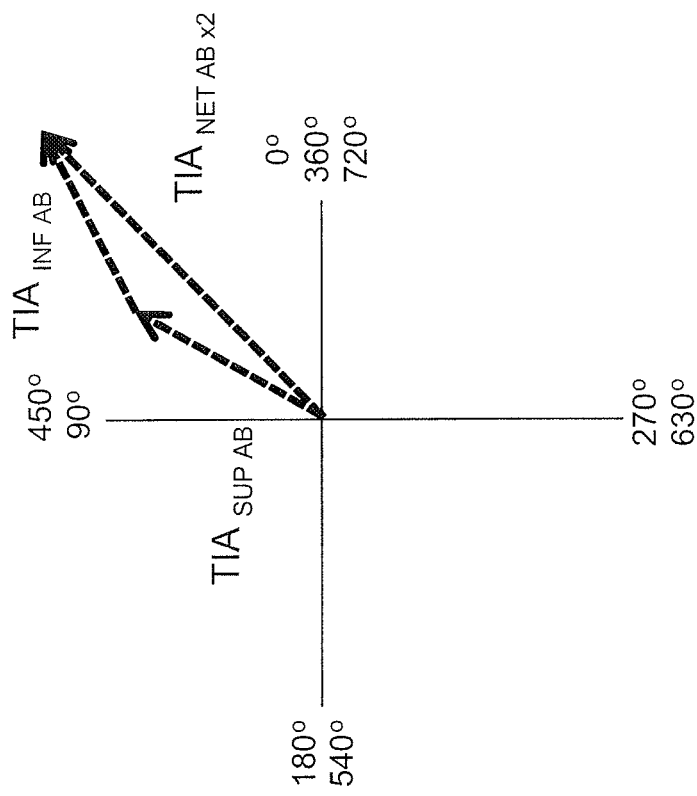
FIG. 10 is a double angle vector diagram showing treatment of the vectors together with magnitudes and axes thereof.
Figure 11A:
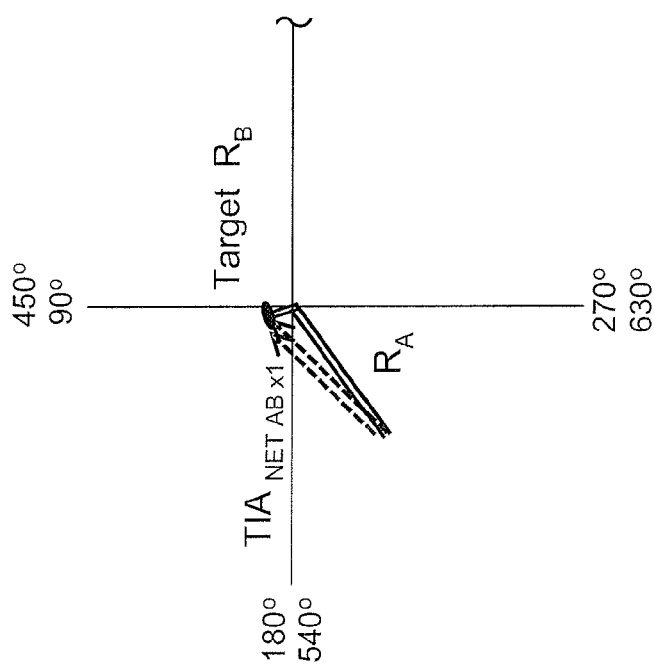
FIG. 11a is a vector diagram illustrating regularization of non-orthogonal astigmatism together with values of magnitude and axes.
Figure 11B:
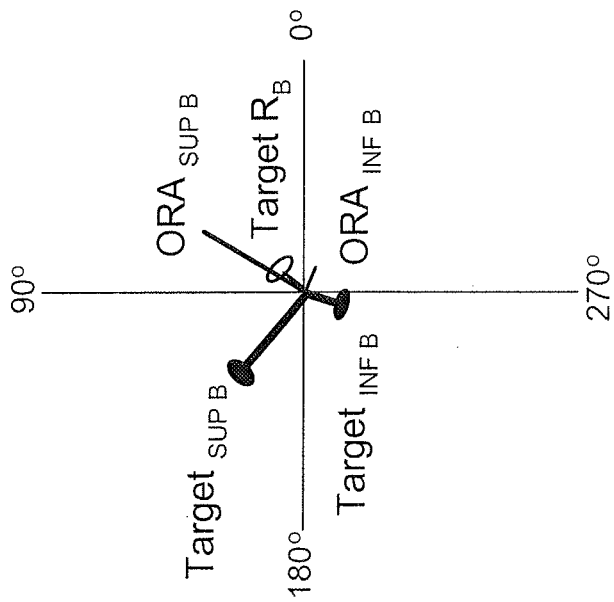
FIG. 11b is a polar diagram showing the refractive and topographic targets including the resultant ORA for each semi-meridian from step AB.

To determine the symmetric refractive cylinder target (Target $R_B$) the net overall treatment effect ($TIA_{NET\ AB\ x2}$) is calculated by summating the applied $TIA_{INF\ AB}$ and the $TIA_{SUP\ AB}$ in a head to tail manner on a DAVD (FIG. 10) FIG. 10 shows DAVD showing summation of optimal treatment vectors $TIA_{SUP\ AB}$ and $TIA_{INF\ AB}$) to calculate average applied treatment ($TIA_{NET\ AB\ x2}$) to refractive astigmatism. The $TIA_{NET\ AB\ X2}$ magnitude is then divided by two due to the addition of the two vectors $TIA_{SUP\ AB}$ and $TIA_{INF\ AB}$. The $TIA_{NET\ AB\ x1}$ (halving the magnitude since two parameters are summated) is then applied to each of the semi meridional displays of the preoperative cylindrical refraction (FIG. 11a displays the orthogonal and symmetrical 'superior' and 'inferior' refractions as a pair—which overlie one another on a DAVD as they are 360° apart) resulting in the one common refractive target (Target $R_B$). This together with the resultant refractive and topographic targets together with the superior and inferior ORA are displayed in FIG. 11b.

This optimized outcome is for the minimum amount of astigmatism to remain—this is equal to the ocular residual astigmatism (ORA) normally addressing the internal aberrations of the whole eye and in this case calculated separately for each semi-meridian.

Regularization Step (Step B to C) with Minimum Remaining ORA

Figure 12A:
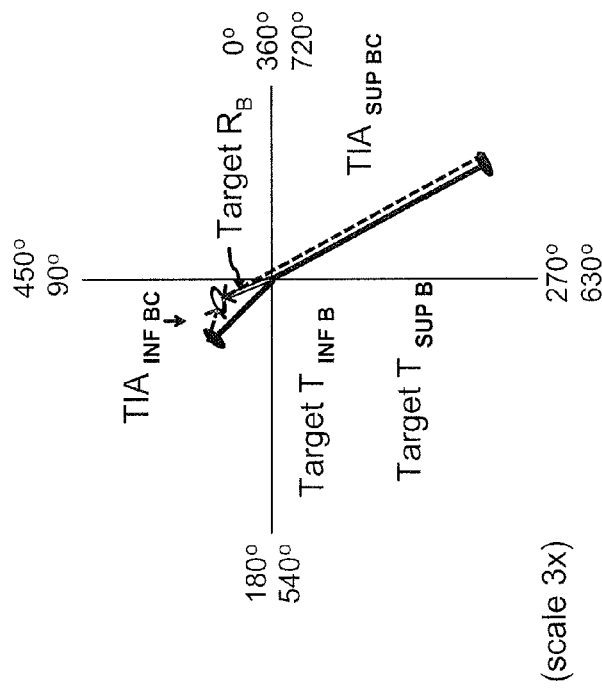
FIG. 12a is a double angle vector diagram showing regularization of non-orthogonal astigmatism after maximum treatment of astigmatism (step AB) by shifting the topography targets to the common refractive target (Target RB) achieved in which this is step B to C (BC).
Figures 13A, 13B:
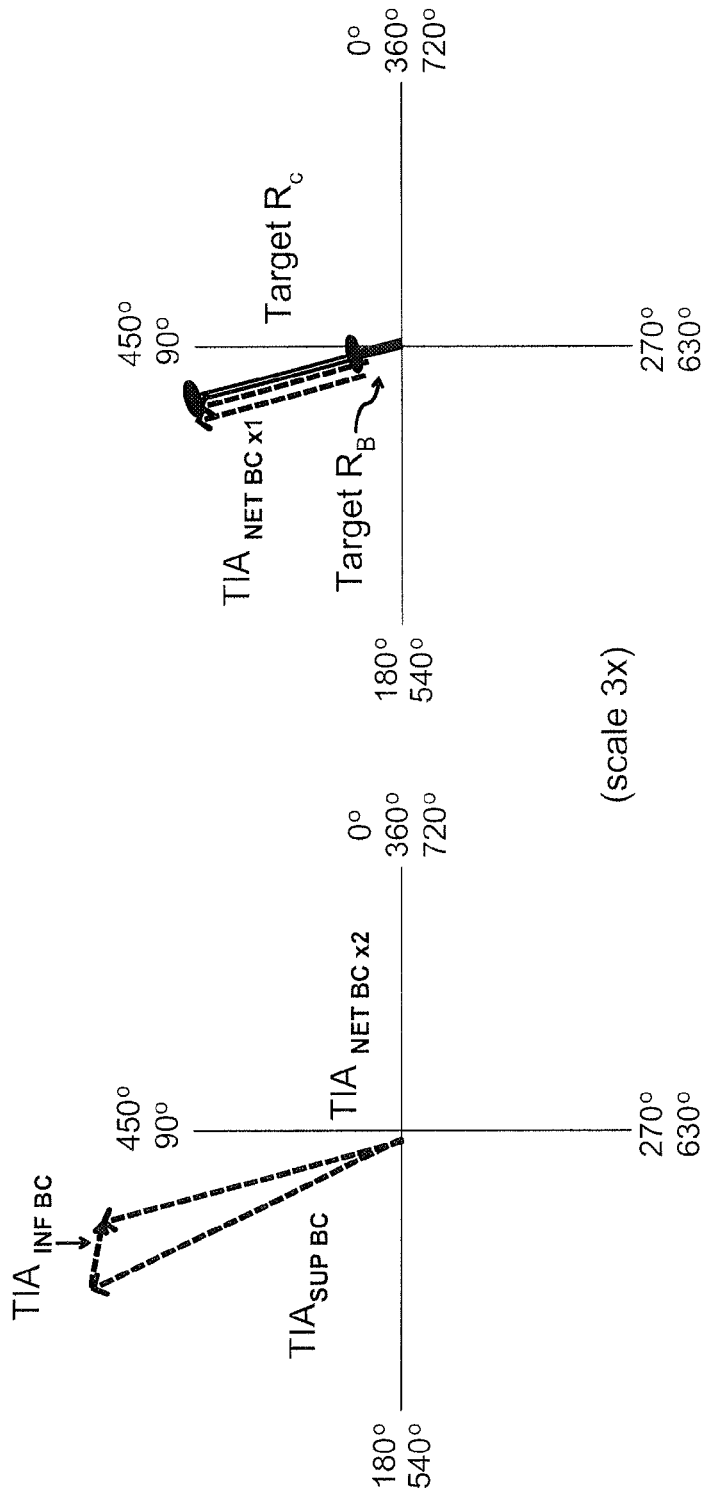
FIG. 13a is a double angle vector diagram showing summation of optimal treatment vectors after regularization.
FIG. 13b is a double angle vector diagram showing applying the average treatment $TIA_{NET\ BCX1}$ to each of the refractive targets (Target $R_B$) to achieve Target $R_C$, in which $TIA_{BCX1}$=ORA at completion of stage 2 (B to C).

A second treatment ($TIA_{SUP\ BC}$ and $TIA_{INF\ BC}$) can then be applied to each corresponding corneal target achieved from the optimal reduction of astigmatism above (Target $T_{SUP\ B}$ and Target $T_{INF\ B}$) to achieve a symmetrical and orthogonal corneal astigmatism outcome This is done by targeting the refractive cylinder target (Target $R_B$) achieved from the first step (step A to B) as shown in FIG. 12a. The resultant refractive targets for the superior and inferior semi-meridian s are displayed in FIG. 12b. The final symmetrical refractive cylinder target (Target $R_C$) from the second step (B to C) of regularization is calculated by again averaging the superior and inferior $TIA_{BC}$ in a head to tail manner and adding this value ($TIA_{NET\ BCx1}$) to Target $R_B$ (FIGS. 13a and 13b) resulting in the common refractive cylinder and the topography being aligned as displayed in FIG. 14.

Figure 14:
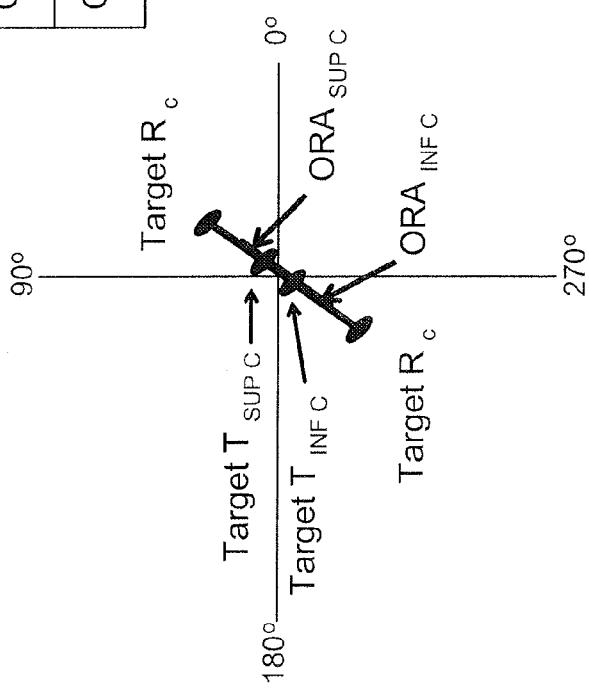
FIG. 14 is a polar diagram showing topography and refractive targets after maximum treatment of astigmatism (AB) and regularization (BC) by shifting the topography targets to the common refractive target (Target RC), in which the ORA in this case is an arithmetic difference between the refractive and topographic targets due to zero difference in axes between the two.

This refractive change from B to C by the treatment $TIA_{NET\ BCx1}$ to each of the Target $R_{B's}$ effectively quantifies each of the separate ORAs ($ORA_C$) to be the minimum possible defined in the same step as regularizing the cornea (FIG. 14).

FIG. 10 shows DAVD showing summation of optimal treatment of the vector together with magnitudes and axes thereof.

Maximum Optimized Reduction and Regularization in One Step (a to C)

Figure 15:
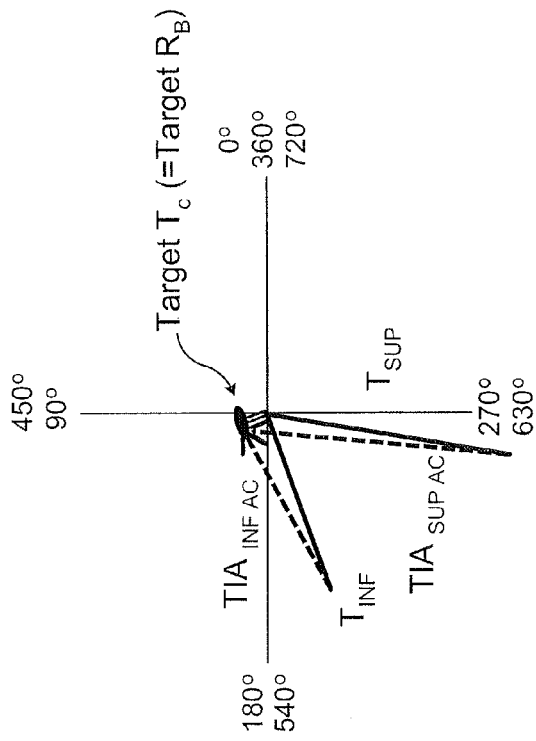
FIG. 15 is a double angle vector diagram showing the treatment applied ($TIA_{SUP\,AC}$ and $TIA_{INF\,AC}$) to the two pre-operative corneal parameters ($T_{SUP\,A}$ and $T_{INF\,A}$) to achieve reduction and regularization of the cornea in one surgical step of the preoperative.
Figure 16:
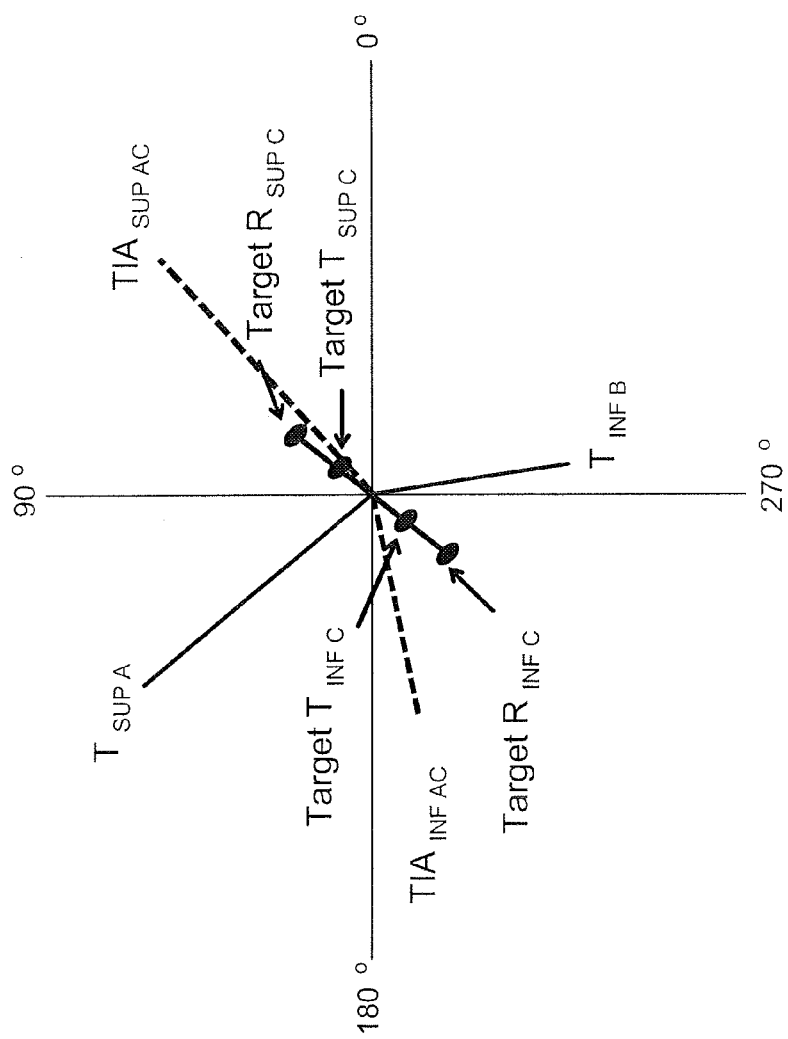
FIG. 16 is a polar diagram showing preoperative topography and with refractive and topographical targets after maximum treatment of astigmatism and regularization in a single surgical step.

The semi-meridian treatments required to achieve in one step the maximum optimized reduction of astigmatism together with a symmetrical, orthogonal cornea ($TIA_{SUP\_AC}$ for superior semi-meridian and $TIA_{INF\_AC}$ for inferior semi-meridian) is calculated by targeting the target refraction from step A to B (Target $R_B$) achieved from the first process of maximally and optimally reducing the existing corneal irregular astigmatism. These treatments are then applied to both the preoperative corneal values ($T_{SUP\_A}$ and $T_{INF\_A}$) as displayed in FIG. 15 to achieve the goal in one surgical treatment step of reduction and regularization. FIG. 16 displays the superior and inferior treatments together with the refractive and topographic targets after maximum treatment of astigmatism and regularization in a single surgical step.

The function of a transparent cornea can be compared to the properties of a clear window pane. Just as warpage in a flat pane of glass causes distortion of transmitted contours for the observer when looking through it, so too does irregularity of the cornea reduce the equally spaced arrangement of parallel light rays that pass through it. The distortion experienced when looking through an irregular cornea can be displayed on an aberrometer using a point spread function of an image of light passing through the cornea with existing elevated high order astigmatisms (HOAs}.

In the commonly practiced symmetrical treatment of corneal astigmatism, whether the astigmatism is regular or irregular, differences commonly exist between corneal and refractive astigmatism values. Conventional treatment by refractive values alone leaves all the non-corneal astigmatism (quantified by the ORA) remaining on the cornea to neutralize the internal aberrations of the eye. This can amount to more than one diopter in more than 30% of eyes treated by laser vision correction for myopia and astigmatism and more than the preoperative existing corneal astigmatism in 7% causing an overall increase in astigmatism as a result of the surgery.

Similarly the net effect of treatment by wavefront parameters alone is an excess of astigmatism left on the corneal surface than is otherwise necessary. A second undesirable effect of aberrometric treatment of HOAs is the necessity to create irregularities on the corneal surface to neutralize those that lie behind it on the light's optical pathway to the retina without specifically attempting to regularize the cornea.

There is no question that wavefront aberrometry is an important and useful diagnostic modality to create an aspheric cornea and improve the spherical visual outcome in patients with large pupils and significant HOAs. However, an inherent disadvantage of the technology is that the aberrations measured and permanently neutralized on the corneal surface may be lenticular or perceptive, and so create a permanent change based on variables that are not stable over time.

The significance of these higher level disorders may be visual cortex and/or occipital perceptions of astigmatism at the visual cortex that influence the manifest refraction is substantially unmeasured and excluded from treatment using aberrometry alone. These non optical astigmatic influences can have a significant effect on the treatment applied to the cornea and its resultant shape when the manifest refraction is the exclusive guiding paradigm. In conventional refractive treatments these are not moderated by any topographic input at all.

There are major theoretical and practical obstacles to the dependence upon wavefront values being used alone as a treatment modality which has also been recognized by other authors. The key benefit of vector planning in the treatment process is the ability to combine preoperative corneal astigmatism parameters with those for refractive wavefront astigmatism in a systematic manner. In this way, the cornea can be protected against astigmatism considered to be unfavorable (such as against-the-rule or oblique), and so avoid excess astigmatism remaining in such cases and its consequent higher order aberrations such as coma or trefoil. Using the technique described, any unavoidable ORA that does remain neutralized on the cornea can be left in an orthogonal symmetric (regular) state, resulting in reduced distortion of parallel light rays as they pass through the cornea. In this manner an optimal visual outcome is possible with both reduced and regularized corneal astigmatism and potentially reduced aberrations.

Figure 8:
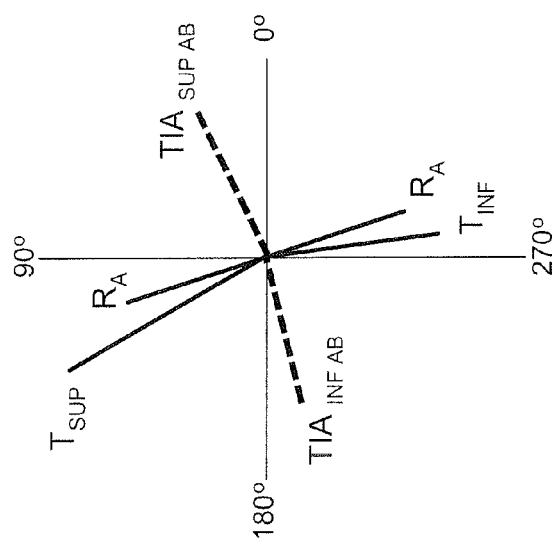
FIG. 8 is a polar diagram illustrating the treatment of astigmatism and the values of various components.

FIGS. 8 and 9 display the maximum reduction of astigmatism. Targeting less corneal astigmatism theoretically shifts a proportion of the remaining astigmatism to the refractive level. In practice this has been shown to be less than expected when actual post operative manifest refractions are measured and evaluated. The vector planning technique employing asymmetrical corneal astigmatism treatments (FIG. 8) attempts to minimize the non-corneal astigmatism, quantified by ORA, hence gaining the maximum correspondence between corneal and refractive values and potentially improve the optical quality of the perceived image. The best possible equivalence between these two is likely to minimize both lower and higher order optical aberrations within the eye. Referring to FIG. 8, the treatment of irregular astigmatism is effected by applying an optimal asymmetric treatment ($TIA_{SUP\_AB}$ and $TIA_{INF\_AB}$) to each corneal semi-meridian. This maximum correction of astigmatism is denoted as step A to B (AB).

It is envisaged that wavefront measurements are likely in future to make it possible to better match two differing refractive values, one for each semi-meridian, with the two separate topographic values on the cornea, hence employing a separate refractive and topographic measurement for each corneal semi-meridian. This combined treatment paradigm has a greater potential for improving the best corrected vector analysis (BCVA) than using wavefront or topography parameters alone. The ideal ablation shape to effectively correct irregular astigmatism will be determined by an ellipse that has modified dimensions for each semi-meridian. The ellipses may be angularly displaced to achieve the non-orthogonal and asymmetrical treatment requirements.

The treatment changes necessary to address these asymmetrical and non-orthogonal values of the cornea are achieved by creating gradual and undulating variations in contour between the principal meridian of the cornea. Smooth continual rather than rough abrupt changes have a greater prospect for being sustained to combat the natural forces of epithelial healing that over time are likely to smooth out any localized applied unevenness.

The method of vector planning can be expanded upon to refine outcomes in cases of irregular astigmatism. Utilizing asymmetrical vector planning with a separate astigmatism treatment plan for each separate semi-meridian of the cornea would likely result in less overall astigmatism and a more regular corneal profile at the completion of a single corneal surgery correcting sphere and irregular cylinder. Incorporation of these algorithms into future excimer laser technology would potentially improve the outcomes currently achieved by the treatment of spherocylinder in laser vision correction.

Calculation of Treatment for Maximum Reduction of Astigmatism and Regularization of Cornea The first step in the process is the maximum reduction of astigmatism and has been referred to as step A to B (AB) and the second step the regularization of the cornea as step B to C (BC).

Preoperative parameters are displayed in FIG. 7a.
Superior topography 2.600 @ 130
Inferior topography 1.900 @ 278
Wavefront refraction −3.240 S 1-1.80 DC×18 (BVD=12.5 mm)

The separate semi-meridian astigmatic treatments ($TIA_{SUP\ AB}$ and $TIA_{INF\ AB}$) are displayed in FIG. 8 and are calculated based on emphasis of 40% sphericizing the cornea 160% sphericizing the refractive cylinder with an existing ORA of 1.82 D Ax 59 for the superior semi-meridian. The inferior semi-meridian treatment is also based on 40% sphericizing the corneal 60% sphericizing the refractive cylinder applied to an existing ORA of 0.67 D Ax 340. Irrespective of the emphasis chosen for the ORA, the maximum amount of astigmatism is being treated in each semi-meridian of the cornea.

The vectorial difference between the preoperative topography and the target topography, as determined by the emphasis on neutralizing the ORA, is equal to the astigmatic treatment (TIA) for each semi-meridian. The topography targets (Target $T_{INF\ B}$ and Target $T_{SUP\ B}$) are displayed in FIG. 9.

When the TIA between the two semi-meridians differs, a summation of the TIA's ($TIA_{NET\ AB}$) or average needs to be calculated (FIG. 10) to determine the combined effect on refractive astigmatism. The average of the treatment vectors, the $TIA_{NET\ AB}$, is calculated using a head to tail summation of the $TIA_{SUP\ AB}$ and $TIA_{INF\ AB}$ which is then divided by 2 because there are 2 values involved in the summation calculation:

$$1.87D\ Ax\ 29 + 1.71D\ Ax\ 194 = 1.730\ Ax\ 22$$

The average treatment vector $TIA_{NET\ AB}$ is added to each of the common pair of refractive values of +1.63 Ax 108 for the 2 semi-meridians (then the axis subsequently is halved to convert to a polar diagram as it would appear on the eye) to obtain a refractive cylinder target ($R_B$) displayed in FIG. 11:

$$1.63\ Ax\ 108 + [+1.73\ Ax\ 22] = +0.25\ Ax\ 53(R_B)$$

To regularize the cornea, the topography targets after the first process of the maximum optimized reduction of astigmatism (Target $T_{INF\ B}$ and Target $T_{SUP\ B}$) (step AB) have a second treatment added ($TIA_{SUP\ BC}$ and $TIA_{INF\ BC}$) to target the initial refractive cylinder result (Target $R_B$) of +0.25 D Ax 53 (axis 106 on DAVD displayed in FIG. 12).

In this example the resultant topography (Target $T_{INF\ C}$ and Target $T_{SUP\ C}$) and the final refraction (Target $R_C$), which again is calculated by vectorially adding the 2 treatments $TIA_{SUP\ BC}$ and $TIA_{INF\ BC}$, are aligned (FIG. 14) resulting in minimum remaining ORA when Target $R_B$ shifts to Target $R_C$ from the resultant net refractive change.

The remaining ORA i.e. the vectorial difference between the final topography and refractive cylinder targets is at a minimum. The topography targets equal 0.25 D @ 53 and result from the maximum reduction of astigmatism and regularization and the effect of the second treatments to regularize the cornea ($TIA_{SUP\ BC}$ and $TIA_{INF\ BC}$). These regularization changes of the second process (BC), affect the refractive target (Target $R_B$)→7 Target $R_C$=0.870 Ax 53 by shifting an amount equal to the resulting final ORA of 0.620 Ax 53.

One Step Treatment for Maximum Reduction and Regularization of Irregular Astigmatism (Step A to C)

The treatment required to maximally reduce (AB) and regularize the astigmatism (BC) in one step begins with the 2 preoperative corneal values ($T_{SUP}$ and $T_{INF}$) targeting the refractive target (Target $R_B$) that is calculated from step AB. The single step treatment here ($TIA_{SUP\ AC}$ and $TIA_{INF\ AC}$ in FIG. 15) is the addition of the TIA superior and TIA inferior treatment vectors calculated in step AB (FIG. 9) and step BC (FIG. 12).

Preoperative parameters
Superior topography 2.600 @ 130
Inferior topography 1.900 @ 278
Treatment
Superior $TIA_{AC}$=2.820 Ax 131 (TIA SUP AB+BC)
Inferior $TIA_{AC}$=1.910 Ax 102 (TIA INF AB+BC)
Targets
Superior topography 0.25 D @ 53
Inferior topography 0.25 D @ 233
Refractive target (Target $R_C$)+0.87 D Ax 53
Symmetrical And Orthogonal Outcome Is Thus Obtained.

Figure 17:
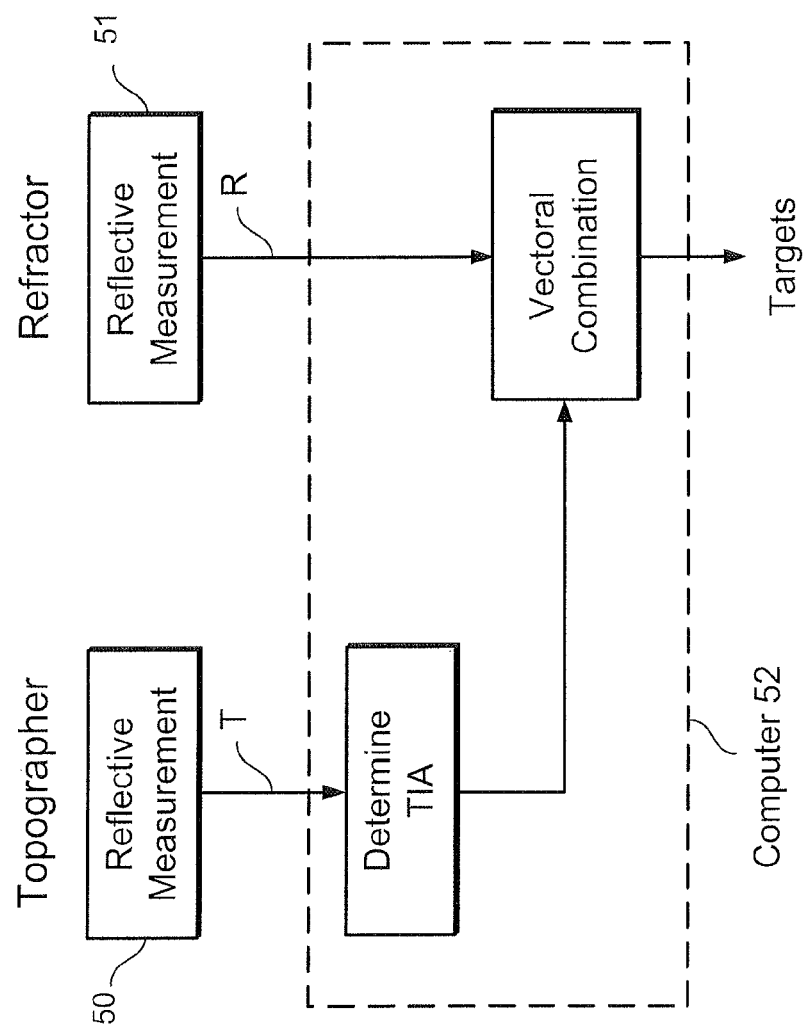
FIG. 17 is a diagrammatic illustration of vector planning apparatus for evaluating and obtaining surgical parameters for treatment of astigmatism in an eye of a patient.

FIG. 17 is a diagrammatic illustration of apparatus for carrying out the methods hereto described.

Therein can be seen a topographer 50 for producing a map of the cornea from which corneal values can be obtained in the 3 mm, 5 mm, and 7 mm zones. FIG. 17 also shows a refractive measuring device which can determine the refractive condition of the eye of a patient. The parameters obtained from the topographer 51 and the refractive measuring device 52 are supplied to computer 53 which carries out the operations heretofore described to produce the topography parameters T sup and T inf as well as TD and CorT and the parameters for TIA sup and TIA inf for the semi-meridians which will provide maximum topographic reduction and minimal ORA.

According to a preferred embodiment to be described hereafter, instead of measuring topographic parameters in the 3, 5 and 7 mm zones, topographic parameters are measured over the entire cornea to obtain CorT values for the entire eye which can be used for vector planning and for obtaining TIA vectors for surgical treatment as previously described.

Figure 18:
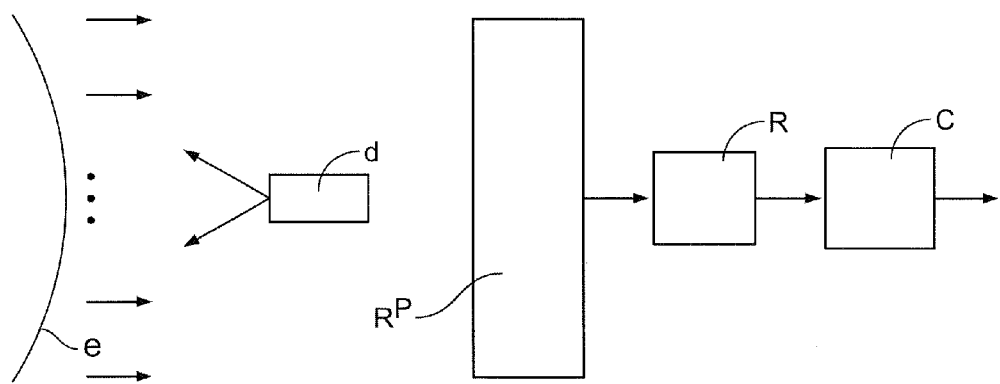
FIG. 18 is a schematic explanatory illustration of apparatus for carrying out the invention.

FIG. 18 diagrammatically illustrates a system for obtaining corneal topography astigmatism values of an eye e of a patient. The eye is illuminated by a device d that generates a multiplicity of concentric circular, so called placido rings r, hereafter referred to simply as rings (shown in FIG. 19). The light from the device d is reflected from the corneal surface of the eye to a photokeratometer scope or camera p that produces an image of the rings corresponding to the shape of the corneal surface of the eye in each ring. The device d and camera p can be combined into a mto a common unit. Another device, such as a computer assisted videokeratographer k reads the image produced by the reflected light from the rings on the cornea from the camera p to produce a multitude of parameters all around each ring. These parameters are input into a central processor unit of a computer c where the parameters are treated according to the invention to produce output results relating to corneal topographic astigmatism.

Figure 19:
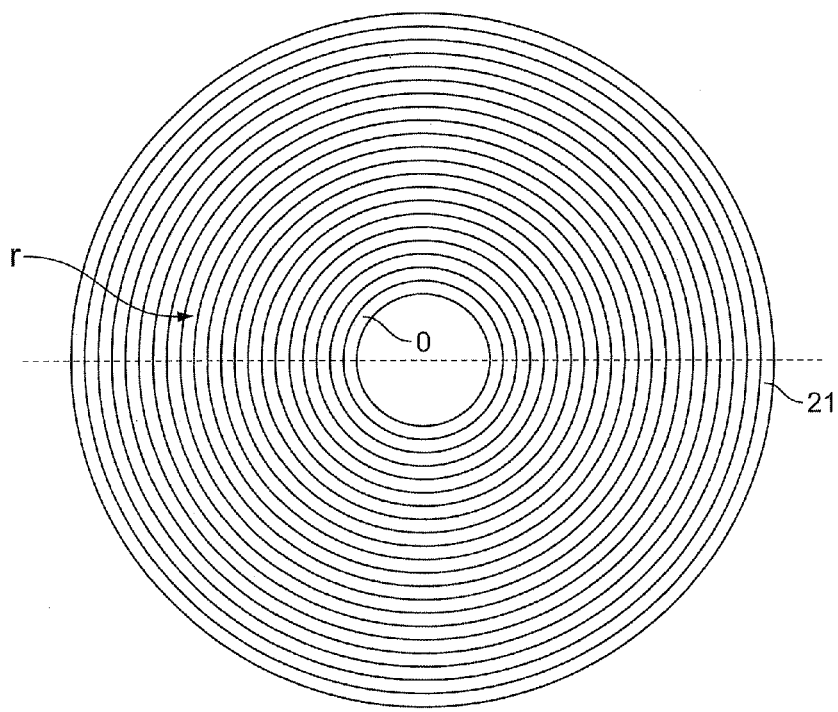
FIG. 19 is a diagrammatic front view of an eye of a patient whose cornea has been illuminated to produce a series of rings on the cornea.

FIG. 19 shows the cornea C in which a multiplicity of rings r are illustrated.

In the particular example, 22 rings are shown but this number can vary, but in general should be at least 0.18 to achieve accurate results. The rings are numbered from 0 to 21 going radially outwards. The rings are concentric around an optical center of the eye and the rings from the device d are uniformly spaced. The rings of light reflected by the cornea become distorted as a function of the corneal astigmatism of the eye. The rings are relatively narrow, of the order of a fraction of a millimeter. The width of the rings is reduced in elevated regions of the corneal surface whereas the width is increased in flatter regions of the rings. The videokeratographer k produces so called axial power measurements of the reflected light from the rings.

The axial power measurements of the reflected light from the rings of a number of patients were obtained using the computer assisted videokeratographer k. For each ring, measurement points were obtained and an astigmatism value was calculated. These ring astigmatism values were combined by vector summation to create a measure termed corneal topographic astigmatism (CorT). This parameter was assessed against other measures of corneal astigmatism, as will be shown later, on how closely each measure matches manifest refractive cylinder.

The flat meridian of the overall CorT can also be used to conceptually divide the cornea into two hemidivisions. A hemidivisional CorT can subsequently be calculated for each hemidivision of the cornea.

In sum, the CorT values of the invention matched manifest refractive cylinder better than three other methods representing the state of the art, namely; manual keratometry, Simulated Keratomery, and corneal wavefront when assessed on: the variance of the magnitude of the ocular residual astigmatism (ORA) across patients, the mean magnitude of the ocular residual astigmatism, and the magnitude of the mean astigmatism measurements.

Accordingly, an alternative measure of corneal astigmatism, according to the invention, derived from topography measurements, known as CorT, corresponds better to manifest refractive cylinder than other commonly used measures. In addition, a hemidivisional CorT can be calculated for each hemidivision of the cornea to effectively represent the non-orthagonal asymmetrical astigmatism in irregular corneas.

When treating astigmatism in refractive laser surgery, it is important that the surgeon not only have an accurate measure of the refractive cylinder but also of the corneal astigmatism. In conventional excimer laser surgery, it is the refractive cylinder that is being ablated onto the cornea, which in many cases is not the same in magnitude and/or orientation as the corneal astigmatism. If these differences are significant, this may lead to suboptimal visual outcomes. The better the correlation between the magnitude and the orientation of the corneal and refractive astigmatism, the less astigmatism will be left remaining in the optical system of the eye as a whole after treatment. The difference between the corneal and refractive astigmatism is precisely described by the ocular residual astigmatism (ORA) and is defined as the vectorial difference between the corneal astigmatism and the refractive astigmatism at the corneal plane. In some cases, the magnitude of corneal astigmatism can increase after excimer laser surgery as a consequence of the treatment being based on refractive parameters alone without considering the amount and orientation of the corneal astigmatism, which results in increasing aberrations and decreasing the visual quality achieved.

Corneal topography heretofore customarily displays a Simulated Keratometry (Sim K) value, which is a quantitative descriptor of corneal astigmatism near the 3 mm zone that was used as an attempt to gain equivalence to corneal keratometry at the time of the introduction of the computer-assisted videokeratography technology in the 1980s.

One commonly encountered difficulty with the Sim K value is that the magnitude and meridian calculated by the device are based on data taken from a narrow annulus in the 3 mm region of the cornea and hence may not be an accurate representation of the existing corneal astigmatism as manifested in refractive cylinder which measures the total astigmatism of the eye including cortical perception. Herein, we describe corneal topographic astigmatism (CorT), which is derived from a wide annular region on the cornea. This measure would ideally correspond to the refractive cylinder, since corneal astigmatism is one of the major contributors to the total astigmatism of the visual system. CorT is also intended to provide a consistent measure of corneal astigmatism across regular and irregular corneas, which can then be implemented in corneal incisional and refractive laser surgery to better correct astigmatism.

Further, we describe an extension of CorT that allows hemidivisional CorTs to be derived for the two hemidivisions of the cornea. These allow a standardized measure of corneal irregularity, known as topographic disparity (TD), to be calculated for non orthogonal asymmetric corneas. The topographic disparity is calculated as the vectorial difference between the two hemidivisional CorTs on a 720 degree double angle vector diagram (DAVD). They are also necessary when assessing and treating particular sections of the cornea with excimer lasers or for the vector planning asymmetric treatment process.

Refractive, keratometric and topographic astigmatism data were assessed retrospectively for a large number of patients. Keratometric data were measured with a Topcon®OM-4 keratometerd. Topographic data were captured with a Zeiss ATLAS™ 9000 kerotographer k and exported using software in the computer. The exported data includes axial curvature measurements at 180 points on 22 rings with varying diameters (widths). The innermost ring (ring 0) has an equivalent diameter on the cornea of approximately 0.8 mm and the outermost ring (ring 21) has an equivalent diameter on the cornea of approximately 11 mm. The rings are spaced almost evenly, except for a slightly increased separation between ring 7 and its two neighboring rings.

The corneal topographic astigmatism (CorT) is calculated as a summated vector mean of the astigmatism values determined from a large number of adjacent rings. Although 22 rings have been shown herein, it has been found that the last three outer rings 19-21 may have abberational errors due to eyelashes and the like and may be discarded. It has also been found that the innermost rings up to ring 12, provide the most accurate results and may be selected for accurate results. In any case, the selected set of rings will be treated as explained hereafter.

First, we determine the astigmatism by finding a best-fit spherocylinder to axial power measurements taken from each single ring. The surface of the spherocylinder will then conform to the corneal surface at the respective ring. We then combine multiple corneal astigmatism parameters via a summated vector mean of the individual values of all the rings.

Taking the axial curvature measurements for a particular ring (ring 7), to fit a spherocylinder to this data it is necessary to perform a least-squares fit of the following form:

$$P(\theta) \sim S + C \cos^2(\theta - M)$$

where the measured power P at meridian $\theta$ is fit with a perfect spherocylinder curve with a spherical component with power S and a cylindrical component with power C and meridian M. Here, if C is positive, then M refers to the steep meridian, but if C is negative, then M refers to the flat meridian. An example of such a fit is shown in FIG. 20.

Figure 20:
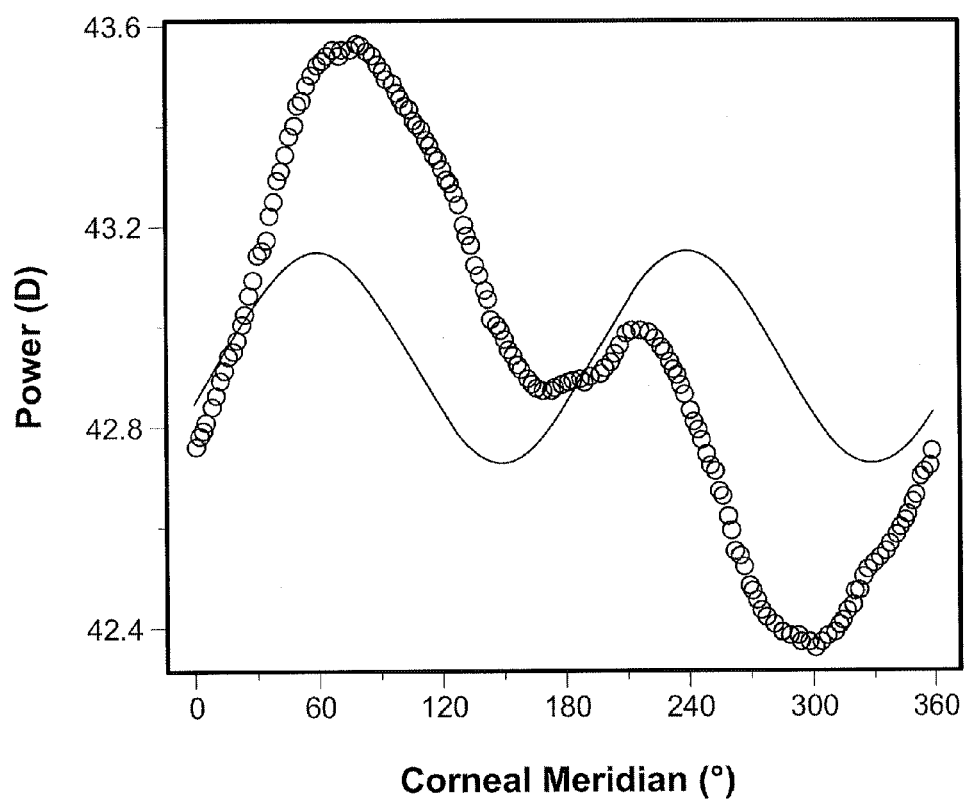
FIG. 20 is a diagrammatic graphical illustration showing a spherocylindrical surface conforming to data from a selected ring.

In FIG. 20 The spherocylindrical curve fits to corneal power data taken from ring 7. The open circles are data, and the continuous line is the spherocylindrical curvet. The data looks substantially different from the fitted curve because the cornea is highly asymmetric.

We call the fitted spherocylinder Ring.#.K (ranging from Ring.0.K to Ring.21.K in this case). Note that the Sim K produced by the Zeiss ATLAS™ 9000 is exactly the same as Ring.7.K.

In order to determine a single parameter of magnitude and meridian representing the corneal astigmatism of each ring, we take the average value of the magnitude at the peak (speepest magnitude) and valley (flattest magnitude) on the spherocylindrical curve and the meridian at the peak.

To calculate a CorT, we need to calculate a summated vector mean of selected Ring.#.Ks. Mathematically, the process is as follows:

1. Represent the cylindrical component of each Ring.#.K as a double angle vector. For a Ring.r.K with a cylindrical component $C_r$ at meridian $M_r$, the double angle vector $v_r$ is $$v_r = (C_r \cos 2M_r, C_r \sin 2M_r)$$

We next calculate the summated vector mean $v_{Mean}$ of the double angle vectors $$v_{Mean} = \frac{\sum_{r \in R} v_r p_r}{\sum_{r \in R} p_r}$$

where R is the set of rings chosen and $p_r$ is the proportion of measurements in ring r that are valid. The presence of the factor $p_r$ ameliorates the influence of missing data on the summated vector mean. If there are no missing measurements in any of the chosen rings, then the summated vector mean reduces to $$V_{Mean} = \frac{\sum_{r \in R} v_r}{|R|}$$

where |R| is the number of rings chosen.

2. We then convert the double angle vector mean back to a cylinder power and meridian $$C_{Mean} = \sqrt{(V_{Mean_x})^2 + (V_{Mean_y})^2}$$

$$M_{Mean} = \frac{1}{2} \tan^{-1} \frac{V_{Mean_y}}{V_{Mean_x}}$$

3. We next calculate the mean keratometric component of the final CorT as an average of the mean keratometric components of the selected Ring.#.Ks $$K_{Mean} = \frac{\sum_{r \in R} K_r}{|R|}$$

In the results section, we determine the rings to be used by performing a complete comparison of all contiguous sets of rings.

Example of Generating a Cort from Multiple Ring.#.Ks

Assume that we want to use only rings 4 and 8 to generate a CorT, and that there are no missing measurements from either ring.

Although in the vector summation of the corneal parameters, the individual ring values will be summated in successive order one after another, hereafter we will describe the vector summation for rings 4 and 8 for illustrative purposes as the differences between any two adjacent rings would be too small to illustrate clearly.

Ring.4.K is 42 D/44 D with the steep meridian @ 100.
Ring.8.K is 42 D/44.5 D with the steep meridian @ 60.

The double angle vectors for the cylindrical components of Ring.4.K and Ring.8.K are (−1.88, −0.68) and (−1.25, 2.17), respectively. The mean is $$\frac{(-1.88, -0.68) + (-1.25, 2.17)}{2} = (-1.56, 0.74)$$

which translates to 1.73 D with the steep meridian @ 77.

The mean keratometry component of CorT is $$\frac{43 + 43.25}{2} = 43.13$$

Therefore, CorT is 42.26/43.99 with the steep meridian @ 77.

Figure 21A:
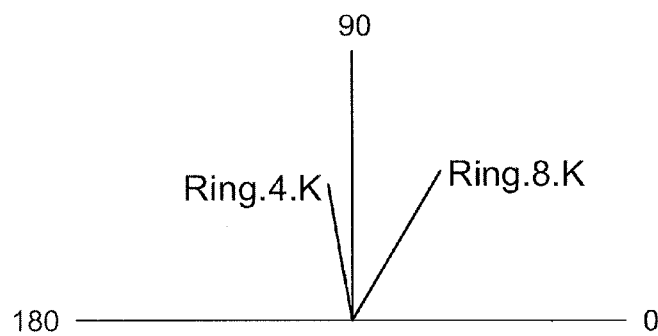
FIG. 21A diagrammatically illustrates magnitude and meridian parameters of two selected rings on a polar diagram.
Figure 21B:
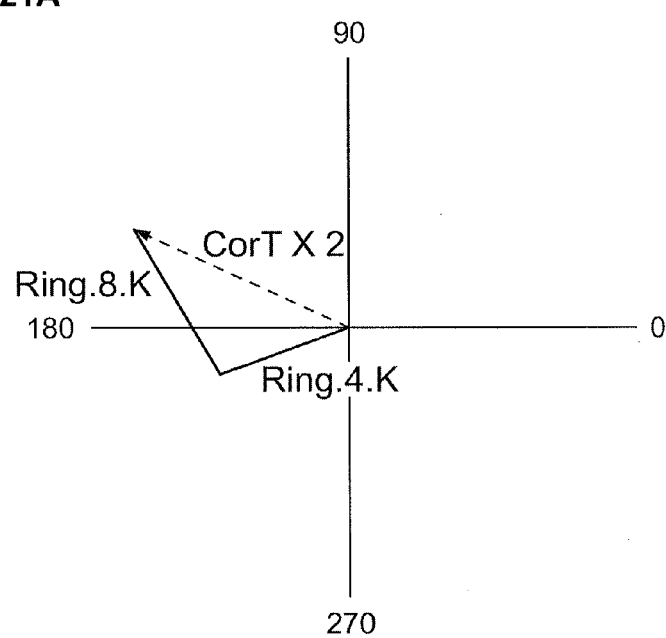
FIG. 21B shows the parameters of FIG. 21A on a double angle vector diagram.
Figure 21C:
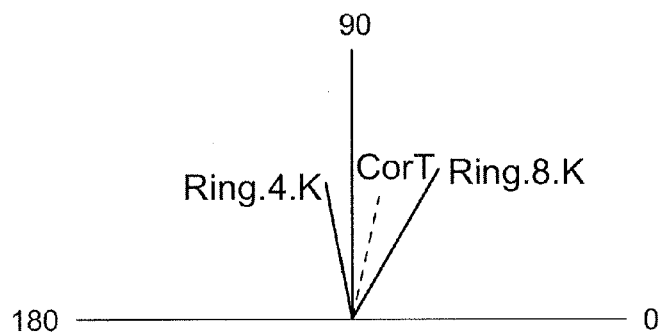
FIG. 21C shows the summated values of the two selected rings on a polar diagram.

This calculation is also shown diagrammatically in FIGS. 21A-21C.

Therein there is shown how the summated vector mean is obtained. The original Ring.#.Ks are shown in FIG. 21A on a polar diagram. FIG. 21B shows a double angle vector diagram showing the Ring.#.Ks as solid lines where the angles have been doubled but the magnitudes remain unchanged. The summated vector sum is shown in FIG. 21C, which in this case of two components is twice the length of the summated vector mean, is shown as a dashed arrow. The resulting actual CorT on a polar diagram, as it would occur on the cornea, is shown as a dashed line half the length displayed in FIG. 21B.

In an earlier patent, I have described dividing an irregular cornea conceptually into two hemidivisions, with two corresponding astigmatisms that have separate, distinct semimeridia. To ensure that this representation is consistent for all corneas, it is necessary to divide the cornea in a functional, systematic way that also works for irregular corneas. If we consider the semimeridia to be aligned in the orientation of the two steep meridia, then an effective way to divide the cornea equally is along the flat meridian of the overall CorT. After dividing the cornea into two hemidivisions, one can calculate hemidivisional Ring.#.Ks and CorTs just like normal Ring.#.Ks and CorTs, except that each calculation is only based on data taken from one hemidivision. The double-angle vector difference between the hemidivisional CorTs is the measure of corneal irregularity known as topographic disparity (TD). Note that the vector mean of the two hemidivisional CorT components is exactly the CorT calculated for the whole cornea.

A known way to generate a representation of corneal astigmatism is from the Zernike coefficients $z_2^2$ and $z_2^{-2}$ of the simulated corneal wavefront data generated by the topographer. Zernike coefficients $z_2^2$ and $z_2^{-2}$ taken together are equivalent to the double angle vector representation of the cylindrical component. The cylinder power and axis are $$C_{wavefront} = \sqrt{(2_2^{-2})^2 + (Z_2^2)^2}$$

$$\theta_{wavefront} = \frac{1}{2} \tan^{-1} \frac{Z_2^{-2}}{Z_2^2}$$

We refer to this representation as corneal wavefront astigmatism (CorW).

Hereafter an evaluation of measures of corneal astigmatism compared to manifest refractive cylinder will be given.

Corneal astigmatism was measured using manual keratometry, computer-assisted videokeratography (Sim K) and corneal wavefront. The CorT value was derived from the axial power data measured by the videokeratograph. To evaluate these four different measures of corneal astigmatism, we calculated the ocular residual astigmatism (ORA) for each of them, which is the vector difference between each measure and the manifest refractive cylinder at the corneal plane. We support the use of manifest refractive cylinder as a benchmark for overall astigmatism as follows:

- manifest refractive cylinder is a measure of the total ocular (corneal and internal) and perceived (visual cortex) cylinder;
- most excimer laser treatments are currently based on manifest refractive parameters, confirming manifest refractive cylinder as the most relevant current measure of visual correction;
- those treatments that are derived from ocular wavefront measurements use manifest refraction as a benchmark for treatment confirmation; and
- eyes with lower ORA magnitudes tend to have better visual outcomes after refractive surgery.

Clinically relevant parameters to compare corneal astigmatism and manifest refractive cylinder measures are next considered.

1. Variability of the ORA Magnitude Determined by Standard Deviation (sd).

Any measure of corneal astigmatism that can be used in corneal and refractive assessment and surgery should preferably match the manifest refractive astigmatism (at the corneal plane). Although the net polar value of the ORA can be described on average by Javal's rule, there is variability of the ORA and its net polar value between eyes. The variability of the ORA magnitude arises from two independent sources: variability in ORA between eyes, and measurement variability (both systematic and random) of the corneal astigmatism and refractive cylinder. For a given set of eyes, we cannot influence the intereye variability, which means that any changes in the variability of the ORA magnitude for this sample must be due to changes in the corneal parameters as the refractive cylinder is common to all four. Any measurement variability trend can be excluded as a factor by examining the summated vector mean which Goggin identified as being random due to its low magnitude. Thus, reduced variability of the ORA magnitude indicates an improved consistency in match between corneal astigmatism and manifest refractive cylinder across different patients, a lower value being preferable. We employ bootstrapping to quantify the amount of variability across different sample populations.

2. Mean Magnitude of the ORA

In clinical practice, the magnitude of the ORA is our principal consideration to evaluate the correlation between corneal and refractive astigmatism, which includes both magnitude and orientation in the assessment. A low magnitude value of ORA indicates closeness of corneal and refractive parameters. This determines what proportion of the preoperative astigmatism can be surgically fully treated (as the ORA will be the amount of astigmatism that will remain in the optical system of the eye either on the cornea or in the manifest refraction or both). We compare the mean ORA magnitudes corresponding to the four different corneal astigmatism measures and their meridia (Man K, Sim K, which is the same as Ring.7.K), CorW and CorT) to determine the correlation to manifest refractive cylinder taking into account both magnitude and axis.

3. Mean Magnitude of Corneal Astigmatism Value Compared to Manifest Refractive Cylinder We determine the corneal astigmatism values that are most representative of refractive function, by comparing these to the magnitude of the manifest refractive cylinder. Here, we specifically look for a close correspondence as further evidence for the validity of the corneal astigmatism magnitude measurements.

Results

In this section, we present the results derived from right eye data in detail. The results from left eye data, which are found to be parallel, are briefly summarized at the end of the results section.

Right Eye Data

We compare the mean ORA for the four corneal measures (man K, Sim K, which is the same as Ring.7.K, CorW and CorT)—specifically the standard deviations of the ORA magnitudes (ORAsd) across patients. A small ORAsd indicates that the corneal measure matches more closely and consistently with the astigmatism benchmark of manifest refractive cylinder than if it were wider. Furthermore for the four corneal measures of astigmatism, we compare the mean magnitude of the ORA and the corneal astigmatism magnitudes to refractive cylinder magnitudes.

To derive CorT, we performed a complete comparison of all contiguous sets of rings to find the set of rings with the lowest ORAsd. To account for any dependence of the ORAsds on our particular sample, we estimated the distribution of the ORAsds from 1000 bootstrap samples. The forty sets of ring groupings with the least variability of the ORA magnitude are shown in Table 1. Ring range 0-17, corresponding to using all available data, has the lowest ORAsd. However, most of the other sets in Table 2 have an ORAsd that is not significantly different to the lowest ORAsd. All of the ring ranges with a low ORAsd include rings 3-8. For our analysis, we generate CorT with ring range 0-17 as it includes all in the range and the least variability.

TABLE 1

Standard deviation of the ORA magnitude for CorT derived from various contiguous sets of rings, as estimated via bootstrapping.

| Ring range | ORAsd mean (D) | 95% confidence interval of difference from "0-17" set | One-sided p-value of difference |
|---|---|---|---|
| 0-17 | 0.331 | — | — |
| 0-16 | 0.332 | (−0.003, 0.004) | 0.42 |
| 0-15 | 0.333 | (−0.005, 0.009) | 0.25 |
| 1-17 | 0.334 | (0.000, 0.006) | 0.02 |
| 1-16 | 0.334 | (−0.001, 0.007) | 0.06 |
| 0-14 | 0.335 | (−0.006, 0.013) | 0.26 |
| 0-13 | 0.335 | (−0.009, 0.017) | 0.29 |
| 0-12 | 0.335 | (−0.011, 0.019) | 0.30 |
| 1-15 | 0.336 | (−0.002, 0.011) | 0.11 |
| 1-12 | 0.336 | (−0.010, 0.019) | 0.28 |
| 1-14 | 0.336 | (−0.005, 0.015) | 0.18 |
| 1-13 | 0.336 | (−0.008, 0.019) | 0.24 |
| 0-11 | 0.337 | (−0.011, 0.024) | 0.27 |
| 1-11 | 0.337 | (−0.011, 0.023) | 0.26 |
| 2-12 | 0.337 | (−0.009, 0.022) | 0.24 |
| 2-11 | 0.337 | (−0.010, 0.023) | 0.25 |
| 2-16 | 0.338 | (0.000, 0.012) | 0.02 |
| 2-13 | 0.338 | (−0.006, 0.021) | 0.17 |
| 2-14 | 0.338 | (−0.003, 0.017) | 0.11 |
| 2-15 | 0.338 | (−0.001, 0.015) | 0.05 |
| 2-17 | 0.338 | (0.001, 0.013) | 0.01 |

TABLE 1-continued

Standard deviation of the ORA magnitude for CorT derived from various contiguous sets of rings, as estimated via bootstrapping.

| Ring range | ORAsd mean (D) | 95% confidence interval of difference from "0-17" set | One-sided p-value of difference |
|---|---|---|---|
| 1-10 | 0.340 | (−0.010, 0.027) | 0.19 |
| 2-10 | 0.340 | (−0.010, 0.026) | 0.19 |
| 0-10 | 0.340 | (−0.009, 0.028) | 0.18 |
| 3-11 | 0.340 | (−0.008, 0.027) | 0.16 |
| 3-12 | 0.340 | (−0.006, 0.025) | 0.13 |
| 2-9 | 0.341 | (−0.010, 0.029) | 0.17 |
| 3-9 | 0.341 | (−0.009, 0.029) | 0.16 |
| 3-10 | 0.341 | (−0.008, 0.028) | 0.15 |
| 1-9 | 0.342 | (−0.008, 0.031) | 0.14 |
| 3-13 | 0.342 | (−0.003, 0.024) | 0.08 |
| 0-9 | 0.342 | (−0.008, 0.030) | 0.12 |
| 3-14 | 0.342 | (0.000, 0.022) | 0.02 |
| 3-15 | 0.343 | (0.002, 0.021) | 0.01 |
| 3-16 | 0.343 | (0.003, 0.020) | 0.00 |
| 3-8 | 0.344 | (−0.008, 0.033) | 0.13 |
| 2-8 | 0.344 | (−0.008, 0.033) | 0.11 |
| 4-9 | 0.344 | (−0.007, 0.033) | 0.11 |
| 4-11 | 0.344 | (−0.004, 0.030) | 0.08 |
| 3-17 | 0.345 | (0.004, 0.022) | 0.00 |

The forty sets of rings shown are those with the lowest standard deviations of the ORA magnitude (ORAsd) for our data set. The third column shows the 95% confidence interval of the difference between the ORAsd for the current ring range and the ORAsd for rings 0-17, and the fourth column shows the corresponding one-sided p-values. For most of the ring ranges shown, the p-value is greater than 0.05, meaning that there is no statistically significant difference at the 5% confidence level.

Figure 22:
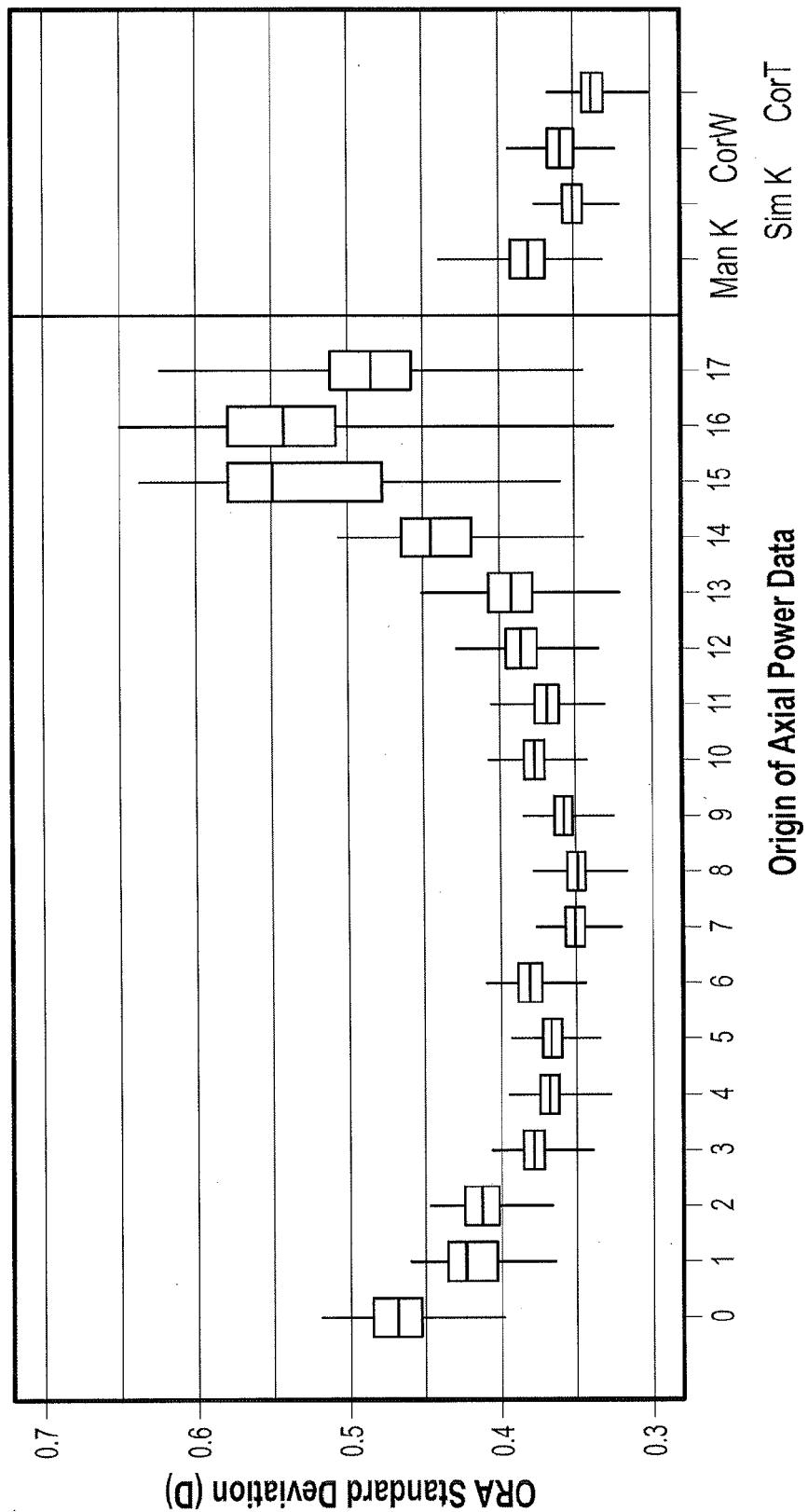
FIG. 22 shows raw axial power data for ring 7 alone and for rings 0-9.

FIG. 22 shows the bootstrapped ORAsd values (estimated from 1000 bootstrap replications) for the Ring.#.Ks, Man K, Sim K, CorW, and CorT. The ORAsd values for the inner Ring.#.Ks (rings 0-2) and for the outer Ring.#.Ks (rings 14-17) are higher and more variable than those for the intermediate Ring.#.Ks (rings 3-13).

FIG. 22 shows the bootstrapped standard deviations of the ORA magnitude. The boxplots labeled 0 to 17 are calculated from the corresponding Ring.#.Ks. The four boxplots labeled Man K, Sim K, CorW and CorT are calculated from manual keratometry, ring 7, corneal wavefront, and CorT derived from rings 0-17, respectively. The boxplots show the quartiles and extremes of the bootstrapped values. CorT has the smallest value, corresponding to a lower variability of the ORA.

Variability of the ORA Magnitude Determined by Standard Deviation (sd)

Table 2 shows confidence intervals for direct comparisons between the ORAsd for CorT and the ORAsds for Man K, Sim K, and CorW. The ORAsd for CorT is significantly lower than that from Man K and CorW, and Sim K.

TABLE 2

Difference between the ORAsd for CorT and the ORAsd for three other corneal measures of astigmatism, as estimated by bootstrapping.

| Comparison | Mean (D) | 95% confidence interval (D) | One-sided p-value |
|---|---|---|---|
| CorT ORAsd − Man K ORAsd | −0.057 | (−0.083, −0.018) | 0.001 |
| CorT ORAsd − Sim K ORAsd | −0.018 | (−0.039, 0.003) | 0.045 |
| CorT ORAsd − CorW ORAsd | −0.026 | (−0.048, −0.003) | 0.014 |

The one-sided p-values correspond to the null hypothesis that the CorT ORAsd is not less than the other ORAsds. The ORAsd for CorT is significantly less than the ORAsd for manual keratometry (Man K), corneal wavefront astigmatism (CorW) and ORAsd derived from ring 7 (Sim K).

Mean ORA magnitudes are shown in Table 3. The CorT ORA values tend to be lower and more consistent (have lower variability) than the ORA values from other corneal measures. The closeness of the ORA summated vector means to the mean ORA magnitudes demonstrates a strong trend for the ORA and little random measurement error.

TABLE 3

Statistics for ORA values.

| | ORA magnitude (D) | ORA summated vector mean (D) | ORA Proportion |
|---|---|---|---|
| Manual keratometry | 0.68 (SD 0.38) | 0.51 × 173 | 75% |
| Simulated keratometry | 0.70 (SD 0.35) | 0.56 × 179 | 80% |
| Corneal wavefront | 0.74 (SD 0.36) | 0.61 × 179 | 82% |
| Corneal topographic astigmatism | 0.62 (SD 0.33) | 0.45 × 178 | 73% |

The first column shows the means and standard deviations of the magnitudes, while the second column has summated vector means, which also considers the orientation of each ORA and the overall trend of the data. The mean and standard deviation of the ORA is lowest for corneal topographic astigmatism, indicating closer correlation to manifest refraction cylinder across patients than the other corneal measures of astigmatism. The summated vector mean of the CorT ORA is the least, which is consistent with the overall trend of best correspondence to manifest refractive values. Proportions in the right column are all of the same order with consistent trends present Mean Magnitude of the ORA In Table 4, a comparison of ORA magnitudes is shown. The ORA magnitudes for CorT are significantly lower than the ORA magnitudes from the three other measures.

TABLE 4

Differences between the magnitude of the ORA generated from CorT and the magnitude of the ORA from Man K, Sim K, and CorW, as estimated by bootstrapping.

| Comparison | Mean (D) | 95% confidence interval (D) | One-sided p-value |
|---|---|---|---|
| CorT ORA magnitude − Man K ORA magnitude | −0.057 | (−0.085, −0.032) | <0.001 |
| CorT ORA magnitude − Sim K ORA magnitude | −0.077 | (−0.097, −0.060) | <0.001 |
| CorT ORA magnitude − CorW ORA magnitude | −0.118 | (−0.139, −0.101) | <0.001 |

The one-sided p-values correspond to the null hypothesis that the CorT ORA magnitude is not less than the other ORA magnitudes. The ORA magnitude generated from CorT is significantly less than the ORA magnitude generated from Man K, Sim K and CorW.

Mean Magnitude of Corneal Astigmatism Compared to Refractive Cylinder

Average values for astigmatism and cylinder are shown in Table 5. The CorT astigmatism values are significantly smaller and closer to manifest refractive cylinder than other corneal measures of astigmatism.

TABLE 5

Statistics for mean astigmatism values.

| | Astigmatism magnitude (D) | One sided p value |
|---|---|---|
| Refractive cylinder at the corneal plane | 0.78 (SD 0.76) | — |
| Manual keratometry | 0.91 (SD 0.74) | <0.001 |
| Simulated keratometry | 0.98 (SD 0.69) | <0.001 |
| Corneal wavefront | 1.06 (SD 0.75) | <0.001 |
| Corneal topographic astigmatism | 0.80 (SD 0.58) | <0.001 |

The first column shows the means and standard deviations of the magnitudes, while the second column has the p-values. Corneal topographic astigmatism has significantly smaller astigmatism magnitudes (all raw bootstrapped p < 0.001).

The mean differences between the astigmatism magnitudes and refractive cylinder are compared in Table 6. The difference between CorT astigmatism magnitude and refractive cylinder is significantly less than the differences of Man K, Sim K and CorW astigmatism magnitudes from refractive cylinder.

TABLE 6

Differences between the mean magnitudes of corneal astigmatism and the mean magnitude of refractive cylinder at the corneal plane, as estimated by bootstrapping.

| Comparison | Mean (D) | 95% confidence interval (D) |
|---|---|---|
| Mean Man K astigmatism magnitude – Mean refractive cylinder magnitude | 0.137 | (0.087, 0.184) |
| Mean Sim K astigmatism magnitude – Mean refractive cylinder magnitude | 0.201 | (0.149, 0.251) |
| Mean CorW astigmatism magnitude – Mean refractive cylinder magnitude | 0.285 | (0.233, 0.336) |
| Mean CorT astigmatism magnitude – Mean refractive cylinder magnitude | 0.018 | (−0.030, 0.069) |

The difference between the mean CorT astigmatism magnitude and the mean refractive cylinder magnitude is significantly lower than the three others.

Left Eye Data

We repeated the analysis reported above with left eye data and obtained parallel results. The best range of rings to generate CorT by examining ORAsd mean is 0-17, and the best forty ring ranges all included rings 4-10. The ORAsds for the intermediate Ring.#.Ks (rings 3-12) are less than those for the inner Ring.#.Ks (rings 0-2) and the outer Ring.#.Ks (rings 13-17). The ORAsd for CorT is significantly less than the ORAsd for Man K, Sim K, and corneal wavefront astigmatism at the 5% confidence level. The mean ORA magnitudes corresponding to Man K, Sim K, CorW and CorT are 0.67 D, 0.69 D, 0.74 D and 0.60 D, respectively, showing that the ORA magnitude for CorT is smallest (all raw bootstrapped p-values<0.001). The mean astigmatism magnitudes corresponding to Man K, Sim K, CorW, and CorT are 0.96 D, 1.02 D, 1.12 D and 0.84 D, respectively, showing that the CorT astigmatism magnitude is the closest to the mean refractive cylinder magnitude which is 0.75 D at the corneal plane.

Example of Generating Hemidivisional CorTs

Figure 23:
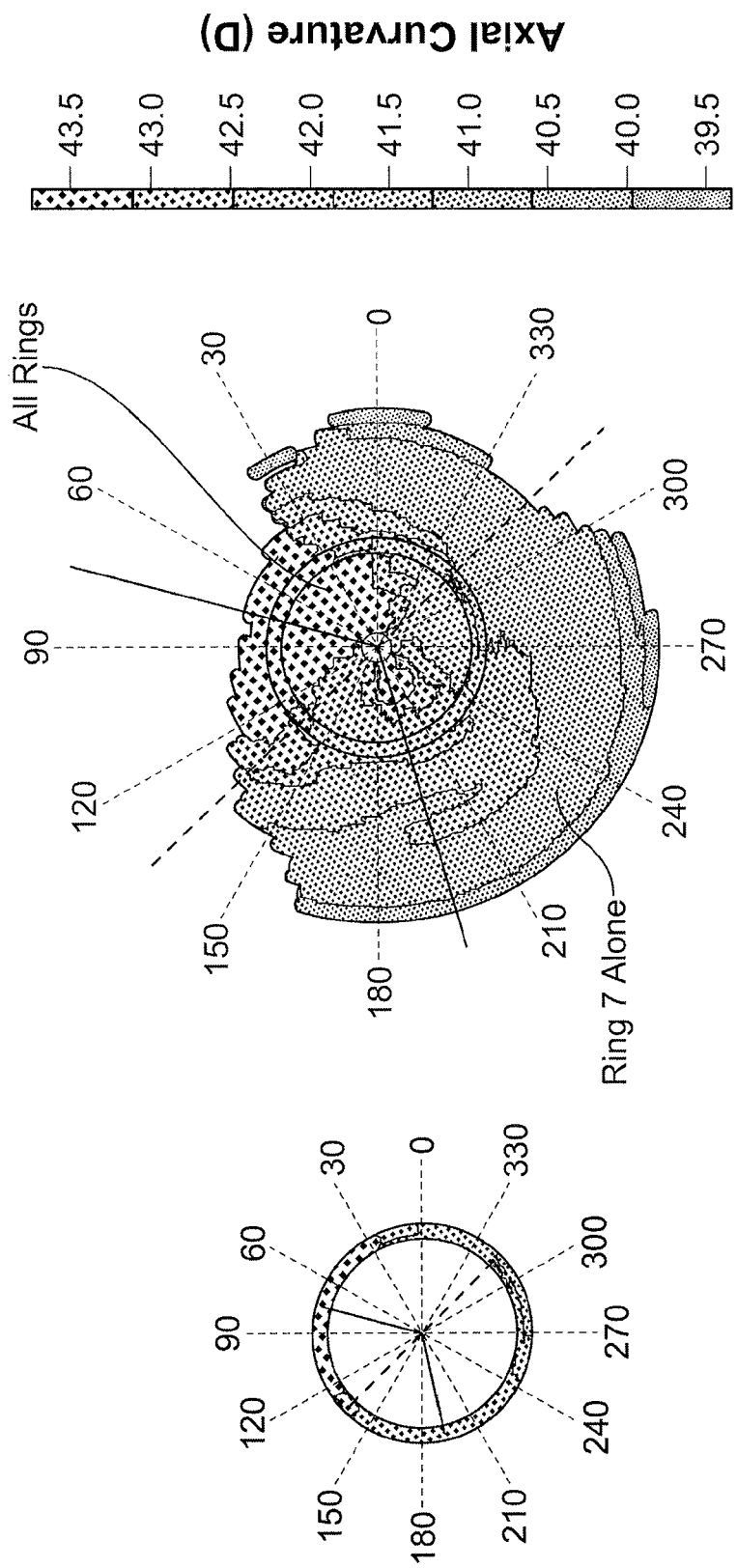
FIG. 23 illustrates bootstrapped standard deviations of the ORA.

In FIG. 23, the axial curvature data for a virgin right eye with irregular astigmatism are displayed. The Ring.#.Ks for this eye are shown in Table 7. For this example, we use equal weightings across all available rings to calculate the overall CorT. The flat meridian of the CorT is @ 134 and 314 degrees, so the cornea is devided here. The new hemidivisional Ring.#.Ks are also shown in Table 7. The semimeridia are shown overlaid on the axial curvature data in FIG. 23. The CorT semimeridia @ 74 and 197 degrees happen to agree with the Sim K semimeridia @ 75 and 193 degrees in this example. Note that the unreliable semi-Ring.#.$K_1$ values for rings 15-17 have a minimal impact on the hemidivisional CorT because of the very small proportion of valid points in each of these semi-rings compared to the whole cornea that CorT takes into account.

FIG. 23 shows axial curvature data. The left image shows ring 7 alone, and the right image shows all measured data. The dashed lines show the division meridian @ 134 and 314 degrees, and the solid lines show the semimeridia of the hemidivisional Ring.7.Ks (left) and CorTs (right).

| Ring number | Proportion of valid measurements | Ring.#.K | | semi-Ring.#.$K_1$ | | semi-Ring.#.$K_2$ | |
|---|---|---|---|---|---|---|---|
| | | Astig. power (D) | Steep meridian (°) | Astig. power (D) | Steep semimeridian (°) | Cyl power (D) | Steep semimeridian (°) |
| 0 | 1.00 | 0.56 | 42.6 | 0.64 | 41.1 | 0.50 | 224.5 |
| 1 | 1.00 | 0.46 | 41.7 | 0.61 | 40.9 | 0.32 | 223.2 |
| 2 | 1.00 | 0.50 | 41.0 | 0.70 | 45.3 | 0.33 | 211.8 |
| 3 | 1.00 | 0.48 | 41.3 | 0.65 | 53.6 | 0.47 | 203.7 |
| 4 | 1.00 | 0.47 | 51.1 | 0.75 | 64.8 | 0.44 | 205.5 |
| 5 | 1.00 | 0.40 | 51.7 | 0.68 | 68.6 | 0.44 | 202.1 |
| 6 | 1.00 | 0.46 | 54.2 | 0.89 | 69.6 | 0.48 | 198.1 |
| 7 | 1.00 | 0.42 | 58.8 | 1.02 | 74.6 | 0.53 | 192.5 |
| 8 | 1.00 | 0.40 | 62.6 | 1.12 | 77.5 | 0.58 | 189.2 |
| 9 | 0.97 | 0.39 | 65.8 | 1.26 | 78.6 | 0.53 | 186.8 |
| 10 | 0.86 | 0.14 | 60.2 | 1.64 | 78.6 | 0.50 | 183.7 |
| 11 | 0.79 | 0.07 | 66.2 | 1.92 | 79.2 | 0.46 | 182.8 |
| 12 | 0.76 | 0.12 | 69.1 | 1.86 | 79.3 | 0.30 | 173.6 |
| 13 | 0.76 | 0.17 | 83.3 | 1.97 | 84.5 | 0.38 | 179.0 |
| 14 | 0.72 | 0.31 | 47.2 | 0.61 | 87.4 | 0.78 | 190.6 |
| 15 | 0.71 | 0.26 | 66.8 | 1.87 | 334.3 | 0.95 | 196.4 |
| 16 | 0.60 | 0.70 | 46.1 | 4.02 | 81.1 | 0.95 | 192.7 |
| 17 | 0.49 | 0.96 | 44.6 | 1.29 | 71.8 | 1.13 | 196.6 |
| 18 | 0.39 | 1.16 | 18.2 | — | — | 1.16 | 198.2 |
| 19 | 0.38 | 1.20 | 17.2 | — | — | 1.20 | 197.2 |
| 20 | 0.37 | 1.30 | 19.9 | — | — | 1.30 | 199.9 |
| 21 | 0.32 | 1.14 | 18.5 | — | — | 1.14 | 198.5 |
| CorT | | 0.40 | 44.2 | 0.94 | 74.4 | 0.54 | 196.7 |

Table 7 shows Ring.#.K and hemidivisional Ring.#.K values corresponding to FIG. 23. The steep meridia of the Ring.#.Ks for the inner four rings is different from those of more peripheral rings. The hemidivisional Ring.#.K semimeridia start out separated by about 180° for ring 0 (see bolded semimeridia in table), but this separation reduces with increasing ring number, until there is a separation of only 94° for ring 12 (see bolded semimeridia at the bottom of the table). Note the unreliability of the semi-Ring.#.Ks when the measured data is fragmentary (e.g., semi-Ring.#.$K_1$ for rings 15-17).

Computer assisted videokeratography provides multiple concentric rings most of which currently do not contribute to quantifying corneal astigmatism as displayed on simulated keratometry.

The combination of these astigmatism values enables the derivation of a value (CorT) that is more representative of the whole cornea by its closer correlation to the manifest refractive cylinder than using parameters derived from manual keratometry, simulated keratometry from the 3 mm zone alone, or corneal wavefront. This reinforces the premise that CorT is an accurate representation of corneal astigmatism when manifest refractive cylinder is the benchmark for assessing the overall astigmatism of the eye. The method described of calculating CorT with its comprehensive inclusion of ring data provides additional safety and accuracy in assessing the suitability of patients for corneal astigmatic surgery including excimer laser, LRIs, toric implants, implantable contact lenses and intracorneal rings.

One of the benefits of using CorT is that the resulting ORA magnitude is lower than that produced by using alternative corneal measures of manual keratometry, simulated keratometry and corneal wavefront astigmatism. This may indicate that estimates of ORA are larger than should normally prevail, because these other measures of corneal astigmatism do not consistently represent the corneal astigmatism that is actually perceived across wider regions of the cornea. However, even when using CorT with the manifest refractive cylinder, there are still outlying eyes that have larger ORA magnitudes than desirable. Magnitudes above 1.00 D may limit the acceptable outcome achievable in correcting astigmatism using refractive parameters alone. For this reason, the surgeon may decide not to treat an eye, treat spherical equivalent only, or to use vector planning, where corneal and refractive parameters are combined in the treatment to optimize and maximally reduce the resultant amount of corneal astigmatism remaining in such cases while avoiding potentially unsatisfactory outcomes. These patients can be counseled prior to surgery that expectations for a complete correction of their existing spherocylindrical refractive error may have to be lowered to realistic levels.

The astigmatism magnitudes for CorT are closest to those for manifest refractive cylinder, which is consistent with our finding that that ORAsd and ORA magnitudes are also lowest using the CorT parameter. This confirms that CorT corresponds better to refractive cylinder than Man K, Sim K, and CorW.

Vector summation of multiple astigmatism values obtained from placido rings for each hemidivision reduces the singular effect of any aberrant measurement, whether it be an artifactual or actual outlier. Outliers might be expected from an automated measurement process such as computer-assisted videokeratography.

Knowledge of both whole-of-cornea and hemidivisional astigmatism values can lead to greater consistency in corneal astigmatism outcomes. The derived hemidivisional values can also be used to calculate the topographic disparity of the cornea. Treatments that might include corneal parameters for either the whole cornea or each hemi division can rely on parameters that have less variability that are currently clinically available. This provides an opportunity to further improve overall visual outcome quality in the routine laser vision correction process.

CONCLUSION

Herein has been described a new method of quantifying corneal astigmatism termed corneal topographic astigmatism (CorT) that corresponds well to manifest refractive cylinder which quantifies the total refractive cylinder of the eye including any cerebral processing. When compared based on the range of the ocular residual astigmatism (ORA) across many eyes, the ORA, magnitude, the standard deviation of the magnitudes and the mean difference between corneal and refractive astigmatism values, demonstrates that CorT aligns significantly more favorably with manifest refractive cylinder than three other commonly used measures of corneal astigmatism: manual keratometry, simulated keratometry, and corneal wavefront astigmatism. We have also described a consistent way of generating two hemidivisional CorT values for a cornea, to allow the astigmatism of the cornea to be considered separately for the two hemidivisions. These two hemidivisional CorT values allow one to derive a value for the topographic disparity, a vectorial measure of corneal irregularity. CorT, ORA, and topographic disparity can be used in the decision making and consent process as fundamental preoperative parameters to help the surgeon to achieve a positive visual outcome when planning astigmatic surgery.

What is claimed is:

1. A method of quantifying corneal topographic astigmatism (CorT) comprising,
    considering at least a portion of an eye of a patient to be divided into a multiplicity of concentric rings,
    forming a curved surface for each ring in which the curved surface conforms to a topography of the cornea of the respective ring,
    determining parameters of the cornea in each ring representative of the corneal topography of the ring, and
    vectorially summating the corneal parameters of all of the rings and obtaining a mean summated vectorial value representing a value of corneal topographic astigmatism (CorT) for said portion of the cornea of the eye of the patient.

2. The method as claimed in claim 1, wherein the curved surface for each ring is formed as a spherocylindrical surface.

3. The method as claimed in claim 2, wherein said spherocylindrical surface is obtained by a method of least squares.

4. The method as claimed in claim 1, wherein said portion of the eye is formed of at least one hemidivision thereof.

5. The method as claimed in claim 4, wherein both hemidivisions of the eye are each considered to be divided into a multiplicity of concentric rings, the sphero-cylindrical surfaces that conform to the corneal topography of the respective ring and provide a topographic map of the respective ring, each ring providing corneal parameters and when the corneal parameters of all of the rings of the respective hemidivision are vectorially summated and a mean value is obtained, a CorT astigmatism value for the hemidivision is obtained so that upon summating the semi-meridian CorT astigmatism values of the two hemidivisions a CorT astigmatism value for the entire eye is obtained that is closer to manifest refractive cylinder than conventional methods.

6. The method as claimed in claim 5, comprising determining the difference between the semi-meridian CorT astigmatism values in the two hemidivisions to obtain topographic disparity (TD) between the two hemidivisions which is a measure of topographic irregularity of the cornea.

7. The method as claimed in claim 2, wherein said rings and said sphero-cylindrical surfaces have a narrow width of a fraction of a millimeter.

8. The method as claimed in claim 1, wherein the multiplicity of rings comprises at least 12 rings.

9. A system for carrying out the method of claim 5 comprising, a device for illuminating a cornea of an eye of a patient to produce a multiplicity of reflected circular rings from the cornea of the eye of the patient, a computer assisted videokeratographer device for receiving of the illuminated rings to produce topographic parameters of the rings of the cornea, and a computer device for producing spherocylindrical curved surfaces in each ring to conform with the corneal surface of the eye and for determining corneal parameters for each ring on the spherocylindrical surfaces and for obtaining a mean vectorial summated value for all of the rings representing semi-meridian CorT astigmatism values for each hemidivision.

10. The system as claimed in claim 9, wherein the computer device additionally performs a subtraction of the semi-meridian CorT values of the two hemidivisions to obtain a value of topographic difference between the two hemidivisions.

11. The system as claimed in claim 9, wherein the computer device vectorially summates the semi-meridian CorT astigmatism values of the two hemidivisions to obtain an overall value of CorT astigmatism for the entire cornea.

12. The method as claimed in claim 1, wherein the multiplicity of rings comprises more than 2 rings.

13. A method of quantifying corneal topographic astigmatism (CorT) that corresponds to manifest refractive cylinder comprising, illuminating a cornea of an eye of a patient over a multiplicity of concentric rings extending from an innermost ring to an outermost ring so that reflected images of the rings provide a topographic map of each of the rings of the cornea, fitting a simulated spherocylindrical curved surface in each said ring which corresponds to the topographic map thereof, selecting topographic parameters from each said ring representative of corneal topographic astigmatism, and vectorially combining selected parameters in the concentric rings to obtain a mean summated topographic value of all of the rings constituting corneal topographic astigmatism (CorT) which corresponds to manifest refractive cylinder.

14. The method as claimed in claim 13, comprising considering the cornea to be divided into two hemidivisions and a separate semi-meridian CorT astigmatism value is obtained for each hemidivision.

15. The method as claimed in claim 14, comprising vectorially subtracting the semi-meridian CorT astigmatism values from one another to obtain a value of topographic disparity (TD) between the two hemidivisions.

16. The method as claimed in claim 13, comprising forming the spherocylindrical surface in each ring by a method of least squares.

17. A method of quantifying corneal topographic astigmatism (CorT) comprising, considering an entire cornea of an eye of a patient to be divided into a multiplicity of concentric rings reflecting off the curved surface of the cornea, wherein each of the rings has a curved surface and the curved surfaces of the respective rings conform to a topography of the cornea, determining parameters of the cornea in each ring representative of the corneal topography of the ring, and vectorially summating the corneal parameters of all of the rings and obtaining a mean summated vectorial value representing a value of corneal topographic astigmatism (Cor T) for said entire cornea of the eye of the patient.

18. A system for carrying out the method of claim 17 comprising, a device for illuminating the cornea of an eye of a patient to produce a multiplicity of reflected circular rings from the cornea of the eye of the patient, a computer assisted videokeratographer device for receiving the illuminated rings to produce topographic parameters of the rings of the cornea, and a computer device for producing spherocylindrical curved surfaces in each ring to conform with the corneal surface of the eye and for determining corneal parameters for each ring on the spherocylindrical surfaces and for obtaining a mean vectorial summated value for all of the rings.

* * * * *